United States Patent
Old

(10) Patent No.: US 9,051,294 B2
(45) Date of Patent: Jun. 9, 2015

(54) THERAPEUTIC AGENTS

(71) Applicant: Allergan, Inc., Irvine, CA (US)

(72) Inventor: David W. Old, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 14/264,144

(22) Filed: Apr. 29, 2014

(65) Prior Publication Data

US 2014/0323558 A1    Oct. 30, 2014

Related U.S. Application Data

(60) Provisional application No. 61/828,801, filed on May 30, 2013, provisional application No. 61/817,586, filed on Apr. 30, 2013.

(51) Int. Cl.
*C07D 333/40* (2006.01)
*C07C 65/36* (2006.01)
*C07C 65/40* (2006.01)

(52) U.S. Cl.
CPC .............. *C07D 333/40* (2013.01); *C07C 65/40* (2013.01); *C07C 65/36* (2013.01); *C07C 2102/08* (2013.01); *C07C 2102/10* (2013.01)

(58) Field of Classification Search
CPC ....... C07D 333/40; C07C 65/36; C07C 65/40
See application file for complete search history.

(56) References Cited

U.S. PATENT DOCUMENTS

| | | | |
|---|---|---|---|
| 4,166,452 | A | 9/1979 | Generales, Jr. |
| 4,256,108 | A | 3/1981 | Theeuwes |
| 4,265,874 | A | 5/1981 | Bonsen et al. |
| 7,427,685 | B2 | 9/2008 | Donde et al. |
| 2011/0184055 | A1 | 7/2011 | Old |

OTHER PUBLICATIONS

Chen et al., 2011, Clin Ophthalmol, 5:667-677.*
Wu, C. et al, Chemical Studies on the Chiral Indanone Derivatives as the Inhibitor of Renilla Luciferase, Tetrahedron, Nov. 19, 2001, 9575-9583, 57(47).
Patent Cooperation Treaty, Notification of Transmittal of the International Search Report and the Written Opinion of the International Searching Authority, or the Declaration, PCT Application No. PCT/US2014/035790, mailed Oct. 1, 2014.
Remington's Pharmaceutical Sciences, Mack Publishing Company, Easton, Pa., 16th Edition, 1980.

* cited by examiner

*Primary Examiner* — Sun Jae Yoo
(74) *Attorney, Agent, or Firm* — Jonathan Y. Bass

(57) ABSTRACT

The invention provides well-defined compounds that are either $EP_2$ agonists, $EP_4$ agonists, or mixed $EP_2/EP_4$ agonist. The compounds are useful for treating a variety of pathological conditions associated with activity of the $EP_2$ and/or $EP_4$ receptors.

11 Claims, No Drawings

THERAPEUTIC AGENTS

CROSS REFERENCE TO RELATED APPLICATION

This application claims the benefit of U.S. Provisional Application Ser. No. 61/828,801, filed May 30, 2013 and U.S. Provisional Application Ser. No. 61/817,586, filed Apr. 30, 2013, the disclosure of which is hereby incorporated in its entirety herein by reference.

FIELD OF THE INVENTION

The present invention relates generally to compounds and methods for treating disorders associated with activity of the $EP_2$ and/or $EP_4$ receptors. The invention relates specifically to the use of certain well-defined compounds for the treatment of ocular hypertension, glaucoma, and skin repair.

BACKGROUND OF THE INVENTION

Prostanoid $EP_4$ receptor is a G protein-coupled receptor that mediates the actions of prostaglandin $E_2$ ($PGE_2$) and is characterized by the longest intracellular C terminus loop when compared to other prostanoid receptors. Mainly, $EP_4$ receptors couple to G proteins and mediate elevations in cAMP concentration, although they do participate in other pathways as well. There are some redundancies in function between $EP_2$ and $EP_4$ receptors. For example, both receptors induce $PGE_2$-mediated RANKL through cAMP. However, $EP_2$ receptors are involved in cumulus expansion in ovulation and fertilization, whereas $EP_4$ regulates closure of the ductus arteriosus. Expression of $EP_4$ receptors is controlled by various physiological and pathophysiological processes as these receptors participate in ovulation and fertilization, induce bone formation, protect against inflammatory bowel disease, facilitate Langerhans cell migration and maturation and mediate joint inflammation in a model of collagen-induced arthritis, among others

SUMMARY OF THE INVENTION

The present invention is directed in part to well-defined compounds that are either $EP_2$ agonists, $EP_4$ agonists, or mixed $EP_2/EP_4$ agonists. These compounds are useful for treating a variety of pathological conditions associated with activity of the $EP_2$ and/or $EP_4$ receptors.

In one embodiment of the invention, there are provided compounds having the structure:

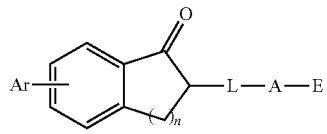

wherein:
Ar is aryl, heteroaryl, substituted aryl, or substituted heteroaryl, wherein substituents are selected from the group consisting of alkyl, alkenyl, alkynyl, hydroxyalkyl, hydroxyl, alkoxy, halogen, —CN, —$CF_3$, —$C(O)R^1$, —$C(O)OR^1$, —$C(O)CF_3$, —$SO_2N(R^1)_2$, —$SO_2NH_2$, or —$NO_2$;
L is $C_1$-$C_6$ alkylene;
A is arylene or heteroarylene;
E is —$CO_2R^1$, —$CH_2OR^1$, —$C(O)N(R^1)_2$, or tetrazol-5-yl;
each $R^1$ is independently H, $C_1$-$C_6$ alkyl, phenyl, or biphenyl; and
n is 0 or 1.
and pharmaceutically acceptable salts thereof.

Another embodiment of the invention includes compositions including at least one compound of the invention, wherein the composition is a liquid which is acceptable for ophthalmic administration.

In another embodiment of the invention there are provided methods of treating a pathological condition associated with $EP_2$ or $EP_4$ receptors. Such methods can be performed for example, by administering to a subject in need thereof a therapeutically effective amount of a composition of the invention. In some embodiments the invention, the pathological condition is glaucoma or elevated intraocular pressure.

In another embodiment of the invention there are provided methods of treating a skin blemish. Such methods can be performed for example, by administering to a subject in need thereof a therapeutically effective amount of a composition of the invention.

Some embodiments of the present invention are included in the following paragraphs:

1) A compound having the structure:

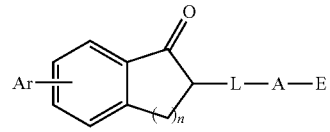

wherein:
Ar is aryl, heteroaryl, substituted aryl, or substituted heteroaryl, wherein substituents are selected from alkyl, alkenyl, alkynyl, hydroxyalkyl, hydroxyl, alkoxy, halogen, —CN, —$CF_3$, —$C(O)R^1$, —$C(O)OR^1$, —$C(O)CF_3$, —$SO_2N(R^1)_2$, —$SO_2NH_2$, or —$NO_2$;
L is $C_1$-$C_6$ alkylene;
A is arylene or heteroarylene;
E is —$CO_2R^1$, —$CH_2OR^1$, —$C(O)N(R^1)_2$, or tetrazol-5-yl;
each $R^1$ is independently H, $C_1$-$C_6$ alkyl, phenyl, or biphenyl; and
n is 0 or 1.
or pharmaceutically acceptable salts thereof.

2) The compound of paragraph 1, wherein Ar is substituted or unsubstituted phenyl or naphthyl.

3) The compound of paragraph 1, wherein the substituents are halogen, alkoxy, or —$CF_3$.

4) The compound of paragraph 1, wherein L is $C_1$-$C_3$ alkylene.

5) The compound of paragraph 1, wherein L is methylene.

6) The compound of paragraph 1, wherein A is phenylene or thiophenylene.

7) The compound of paragraph 1, wherein E is —$CO_2R^1$.

8) The compound of paragraph 7, wherein $R^1$ is H or $C_1$-$C_6$ alkyl.

9) The compound of paragraphs 1-8, selected from the group consisting of:
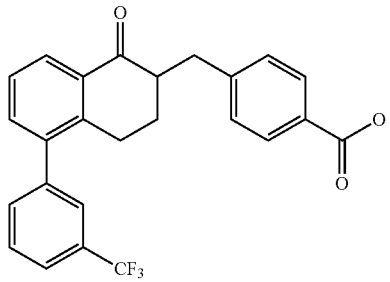
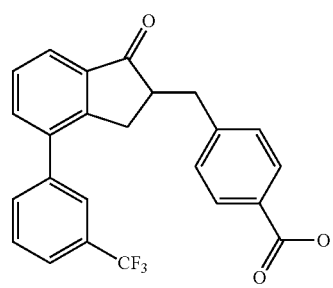
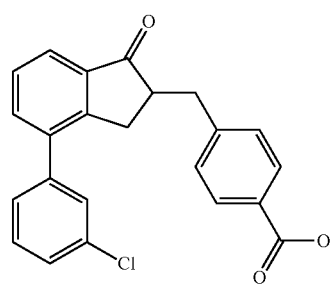
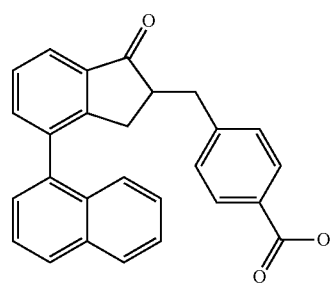
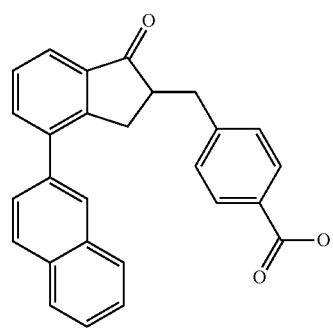
-continued
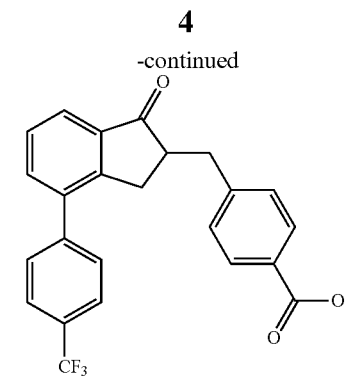
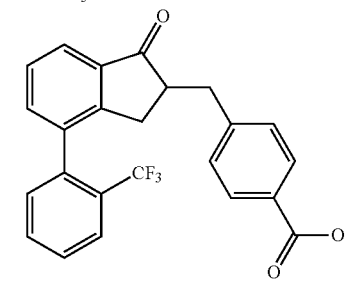
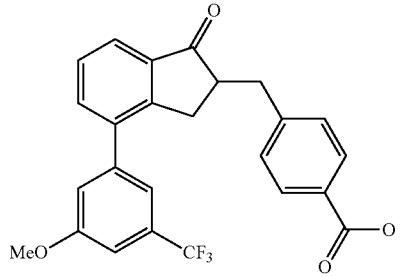
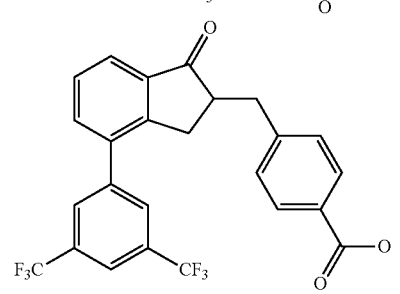
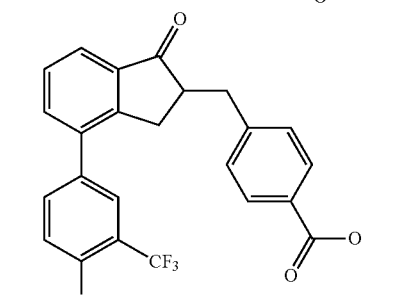
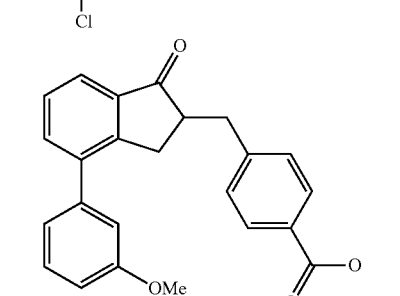

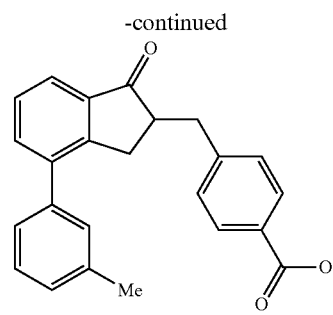

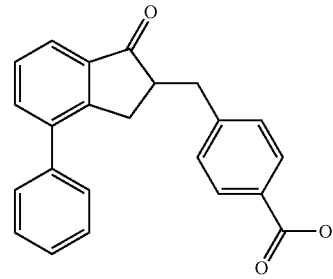

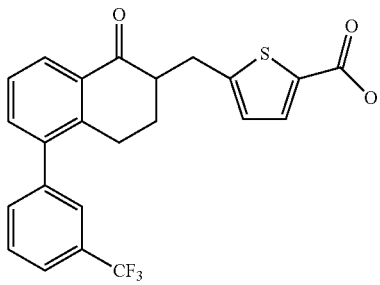

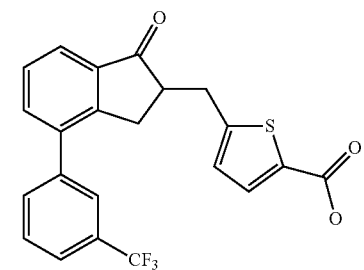

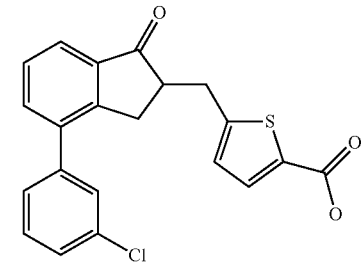

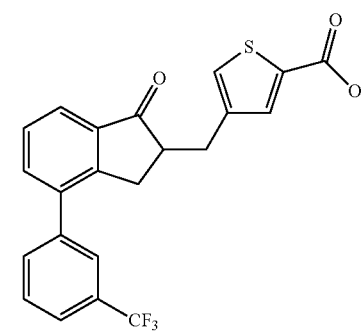

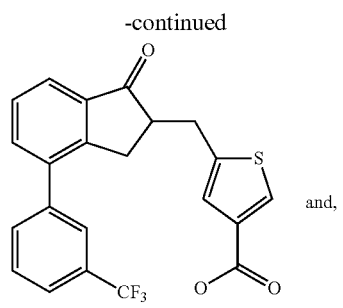

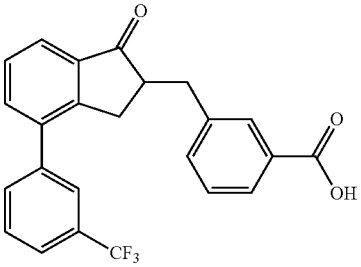

10) A compound having the structure:

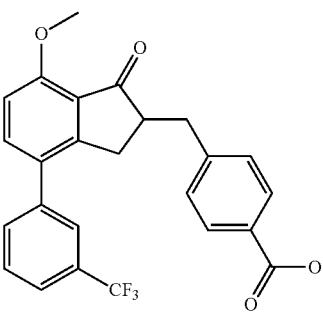 [SMILES: COc1ccc(-c2cccc(C(F)(F)F)c2)c2c1C(=O)C(Cc1ccc(C(=O)O)cc1)C2]

11) A pharmaceutical composition comprising at least one compound according to paragraph 1, and a pharmaceutically acceptable carrier therefor.

12) A method of treating a pathological condition associated with $EP_2$ or $EP_4$ receptors, comprising administering to a subject in need thereof a therapeutically effective amount of the composition according to paragraph 11.

13) The method of paragraph 12, wherein the pathological condition is acute hepatitis, asthma, bronchitis, burn, chronic obstructive respiratory diseases, Crohn's disease, digestive ulcer, glaucoma (and other diseases related to elevated intraocular pressure), hemophagous syndrome, hepatopathy, hypercytokinemia at dialysis, hypertension, immunological diseases (autoimmune diseases, organ transplantation, etc.), inflammation (such as rheumatoid arthritis), Kawasaki disease, liver injury, macrophage activation syndrome, myocardial ischemia, nephritis, nerve cell death, osteoporosis and diseases associated with bone disorders, premature birth, pulmonary emphysema, pulmonary fibrosis, pulmonary injury, renal failure, sepsis, sexual dysfunction, shock, sleep disorder, Still disease, stomatitis, systemic granuloma, systemic inflammatory syndrome, thrombosis and stroke, or ulcerative colitis.

14) The method of paragraph 12 wherein the pathological condition is glaucoma.

15) A method of treating a skin blemish comprising administering to a subject in need thereof a therapeutically effective amount of at least one compound having a structure:

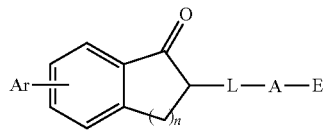

wherein:
   Ar is aryl, heteroaryl, substituted aryl, or substituted heteroaryl, wherein substituents are selected from alkyl, alkenyl, alkynyl, hydroxyalkyl, hydroxyl, alkoxy, halogen, —CN, —CF$_3$, —C(O)R$^1$, —C(O)OR$^1$, —C(O)CF$_3$, —SO$_2$N(R$^1$)$_2$, —SO$_2$NH$_2$, or —NO$_2$;
   L is C$_1$-C$_6$ alkylene;
   A is arylene or heteroarylene;
   E is —CO$_2$R$^1$, —CH$_2$OR$^1$, —C(O)N(R$^1$)$_2$, or tetrazol-5-yl;
   each R$^1$ is independently H, C$_1$-C$_6$ alkyl, phenyl, or biphenyl; and
   n is 0 or 1.
or pharmaceutically acceptable salts thereof.

16) The method of paragraph 15, wherein the skin blemish is a flesh wound, scar, or wrinkle.

17) The method of paragraph 15, wherein the skin blemish is a scar.

18) The method of paragraph 17, wherein the administration minimizes scar formation.

19) The method of paragraph 17, wherein the administration prevents scar formation.

20) The method of paragraph 15, wherein the administration reduces formation of a scar type selected from the group consisting of hypertrophic scar, recessed scar, stretch mark, and a combination thereof.

21) The method of paragraph 16, wherein the skin blemish is a flesh wound.

22) The method of paragraph 21, wherein a cause of the flesh wound is selected from the group consisting of an incision, a laceration, a thermal burn, a chemical burn, an abrasion, a puncture wound, and a combination thereof.

DETAILED DESCRIPTION OF THE INVENTION

It is to be understood that both the foregoing general description and the following detailed description are exemplary and explanatory only and are not restrictive of the invention claimed. As used herein, the use of the singular includes the plural unless specifically stated otherwise. As used herein, "or" means "and/or" unless stated otherwise. Furthermore, use of the term "including" as well as other forms, such as "includes," and "included," is not limiting. The section headings used herein are for organizational purposes only and are not to be construed as limiting the subject matter described.

Unless specific definitions are provided, the nomenclatures utilized in connection with, and the laboratory procedures and techniques of analytical chemistry, synthetic organic and inorganic chemistry described herein are those known in the art. Standard chemical symbols are used interchangeably with the full names represented by such symbols. Thus, for example, the terms "hydrogen" and "H" are understood to have identical meaning. Standard techniques may be used for chemical syntheses, chemical analyses, and formulation.

As used herein, "alkyl" refers to straight or branched chain hydrocarbyl groups having from 1 up to about 100 carbon atoms. Whenever it appears herein, a numerical range, such as "1 to 100" or "C$_1$-C$_{100}$", refers to each integer in the given range; e.g., "C$_1$-C$_{100}$ alkyl" means that an alkyl group may comprise only 1 carbon atom, 2 carbon atoms, 3 carbon atoms, etc., up to and including 100 carbon atoms, although the term "alkyl" also includes instances where no numerical range of carbon atoms is designated. "Substituted alkyl" refers to alkyl moieties bearing substituents including alkyl, alkenyl, alkynyl, hydroxy, oxo, alkoxy, mercapto, cycloalkyl, substituted cycloalkyl, heterocyclic, substituted heterocyclic, aryl, substituted aryl, heteroaryl, substituted heteroaryl, aryloxy, substituted aryloxy, halogen, haloalkyl, cyano, nitro, nitrone, amino, lower alkylamino, lower alkyldiamino, amido, azido, —C(O)H, —C(O)R$_7$, —CH$_2$OR$_7$, —C(O)—, —C(O)—, —S—, —S(O)$_2$, —OC(O)—O—, wherein R$_7$ is H or lower alkyl, acyl, oxyacyl, carboxyl, carbamate, sulfonyl, sulfonamide, sulfuryl, and the like. As used herein, "lower alkyl" refers to alkyl moieties having from 1 to about 6 carbon atoms.

As used herein, "alkenyl" refers to straight or branched chain hydrocarbyl groups having at least one carbon-carbon double bond, and having in the range of about 2 up to about 100 carbon atoms, and "substituted alkenyl" refers to alkenyl groups further bearing one or more substituents as set forth above. As used herein, "lower alkenyl" refers to alkenyl moieties having from 2 to about 6 carbon atoms.

As used herein, "alkynyl" refers to straight or branched chain hydrocarbyl groups having at least one carbon-carbon triple bond, and having in the range of about 2 up to about 100 carbon atoms, and "substituted alkynyl" refers to alkynyl groups further bearing one or more substituents as set forth above. As used herein, "lower alkynyl" refers to alkynyl moieties having from 2 to about 6 carbon atoms.

As used herein, "cycloalkyl" refers to cyclic (i.e., ring-containing) alkyl moieties typically containing in the range of about 3 up to about 8 carbon atoms, and "substituted cycloalkyl" refers to cycloalkyl groups further bearing one or more substituents as set forth above.

As used herein, "aryl" refers to aromatic groups having in the range of 5 up to 14 carbon atoms and "substituted aryl" refers to aryl groups further bearing one or more substituents as set forth above.

As used herein, "heteroaryl" refers to aromatic moieties containing one or more heteroatoms (e.g., N, O, S, or the like) as part of the ring structure and having in the range of 5 up to 14 total atoms in the ring structure (i.e., carbon atoms and heteroatoms). "Substituted heterocyclic" refers to heterocyclic groups further bearing one or more substituents as set forth above.

As used herein, "heterocyclic" refers to non-aromatic cyclic (i.e., ring-containing) groups containing one or more heteroatoms (e.g., N, O, S, or the like) as part of the ring structure, and having in the range of 3 up to 14 carbon atoms and "substituted heterocyclic" refers to heterocyclic groups further bearing one or more substituents as set forth above.

As used herein, "halogen" or "halide" refers to fluoride, chloride, bromide or iodide. "Fluoride, chloride, bromide or iodide" may also be referred to as "fluoro, chloro, bromo, or iodo".

As used herein "arylene" and "heteroarylene" refers to an aryl ring or ring system or a heteroaryl ring or ring system which connects two other parts of a molecule, i.e. the two parts are bonded to the ring in two distinct ring positions. Arylene or heteroarylene may be substituted or unsubstituted. Unsubstituted arylene or heteroarylene has no substituents other than the two parts of the molecule it connects. Substituted arylene or heteroarylene has substituents in addition to the two parts of the molecule it connects.

As used herein tetrazol-5-yl refers to a moiety having the tautomeric forms depicted below:

The two tautomeric forms rapidly interconvert in aqueous or biological media and are thus equivalent to one another.

It will be readily apparent to those skilled in the art that some of the compounds of the invention may contain one or more asymmetric centers, such that the compounds may exist in enantiomeric as well as in diastereomeric forms. Unless it is specifically noted otherwise, the scope of the present invention includes all enantiomers, diastereomers and racemic mixtures. Some of the compounds of the invention may form salts with pharmaceutically acceptable acids or bases, and such pharmaceutically acceptable salts of the compounds described herein are also within the scope of the invention.

A "pharmaceutically acceptable salt" is any salt that retains the activity of the parent compound and does not impart any additional deleterious or untoward effects on the subject to which it is administered and in the context in which it is administered compared to the parent compound. A pharmaceutically acceptable salt also refers to any salt which may form in vivo as a result of administration of an acid, another salt, or a prodrug which is converted into an acid or salt.

Pharmaceutically acceptable salts of acidic functional groups may be derived from organic or inorganic bases. The salt may comprise a mono or polyvalent ion. Of particular interest are the inorganic ions, lithium, sodium, potassium, calcium, and magnesium. Organic salts may be made with amines, particularly ammonium salts such as mono-, di- and trialkyl amines or ethanol amines Salts may also be formed with caffeine, tromethamine and similar molecules. Hydrochloric acid or some other pharmaceutically acceptable acid may form a salt with a compound that includes a basic group, such as an amine or a pyridine ring.

A "prodrug" is a compound which is converted to a therapeutically active compound after administration, and the term should be interpreted as broadly herein as is generally understood in the art. While not intending to limit the scope of the invention, conversion may occur by hydrolysis of an ester group or some other biologically labile group. Generally, but not necessarily, a prodrug is inactive or less active than the therapeutically active compound to which it is converted.

The invention provides compounds having the structure:

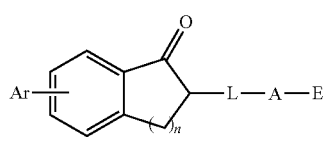

wherein:
Ar is aryl, heteroaryl, substituted aryl, or substituted heteroaryl, wherein substituents are selected from alkyl, alkenyl, alkynyl, hydroxyalkyl, hydroxyl, alkoxy, halogen, —CN, —$CF_3$, —C(O)$R^1$, —C(O)O$R^1$, —C(O)$CF_3$, —$SO_2$N($R^1$)$_2$, —$SO_2NH_2$, or —$NO_2$;

L is $C_1$-$C_6$ alkylene;
A is arylene or heteroarylene;
E is —$CO_2R^1$, —$CH_2OR^1$, —C(O)N($R^1$)$_2$, or tetrazol-5-yl;
each $R^1$ is independently H, $C_1$-$C_6$ alkyl, phenyl, or biphenyl; and
n is 0 or 1.
or pharmaceutically acceptable salts thereof.

In some embodiments of the invention, Ar is substituted or unsubstituted phenyl or naphthyl.

In some embodiments, the substituents are halogen, alkoxy, or —$CF_3$.

In some embodiments, L is $C_1$-$C_3$ alkylene. In certain embodiments, L is methylene.

In some embodiments, A is phenylene or thiophenylene.

In some embodiments, E is —$CO_2R^1$. In certain embodiments, $R^1$ is H or $C_1$-$C_6$ alkyl.

Exemplary compounds according to the invention include, but are not limited to, compounds having any one of the following structures:

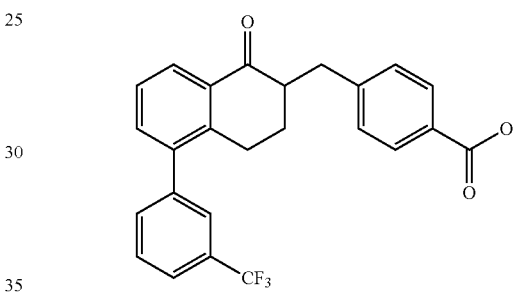

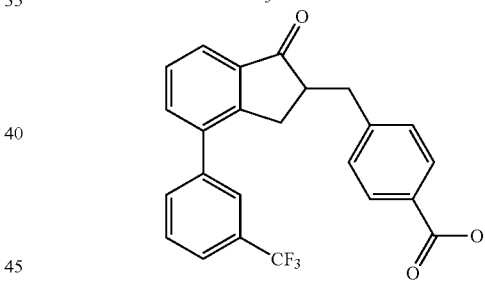

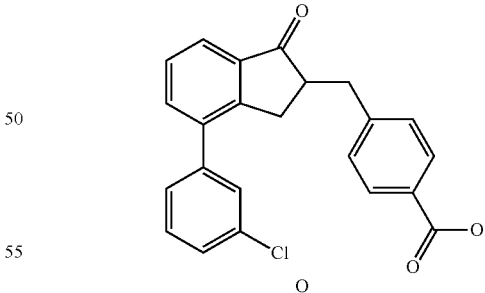

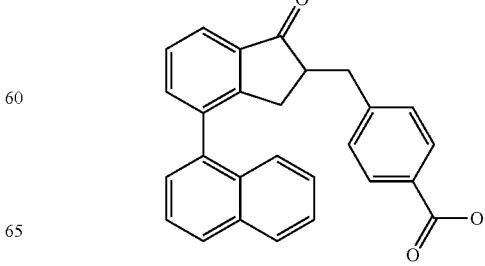

-continued
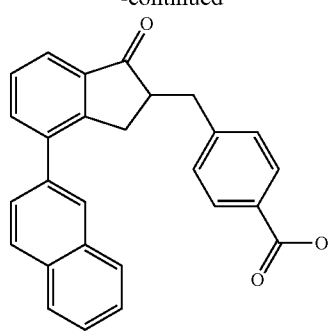
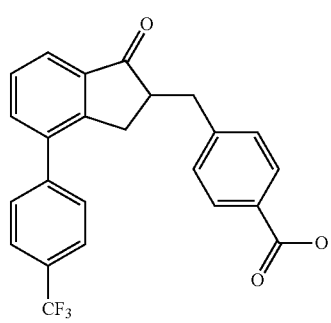
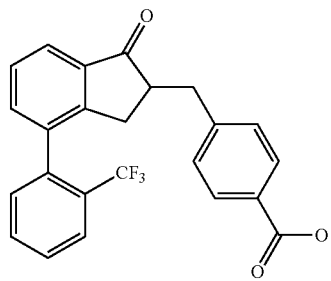
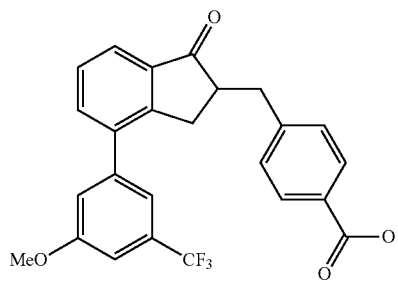
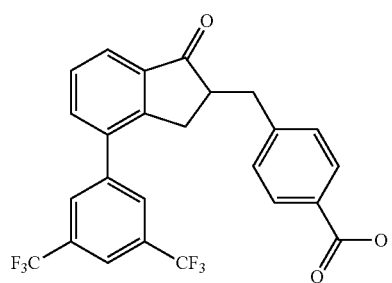
-continued
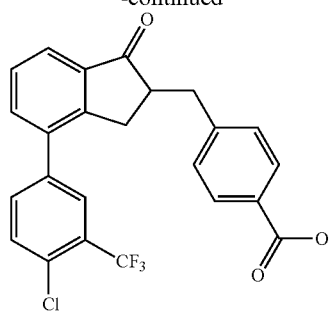
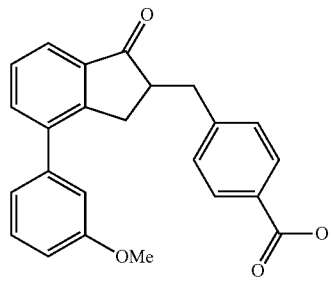
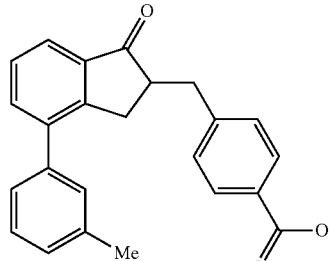
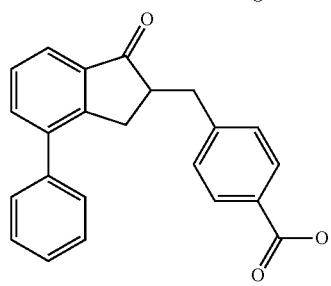
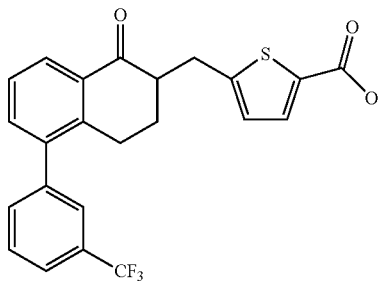
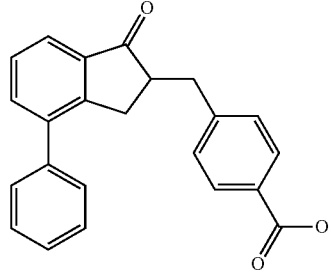

13
-continued
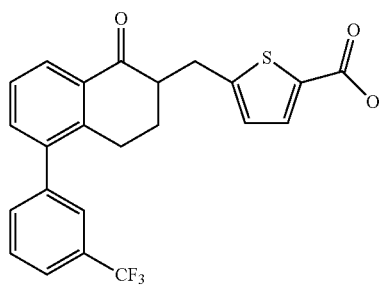
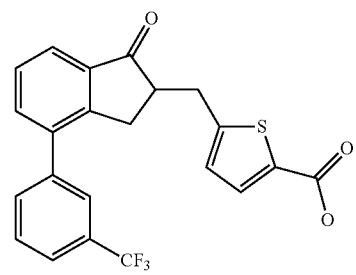
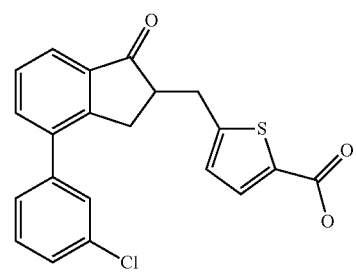
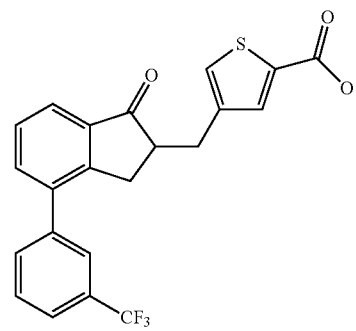
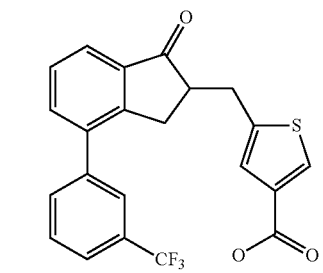
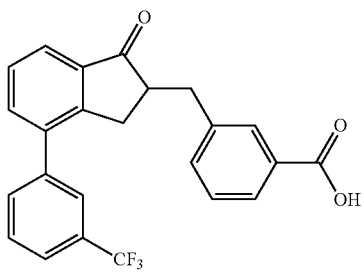
14
-continued
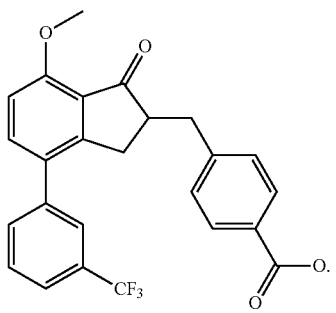
Scheme 1 sets forth below outlines a synthetic route to the compound of the invention described in Example 1:
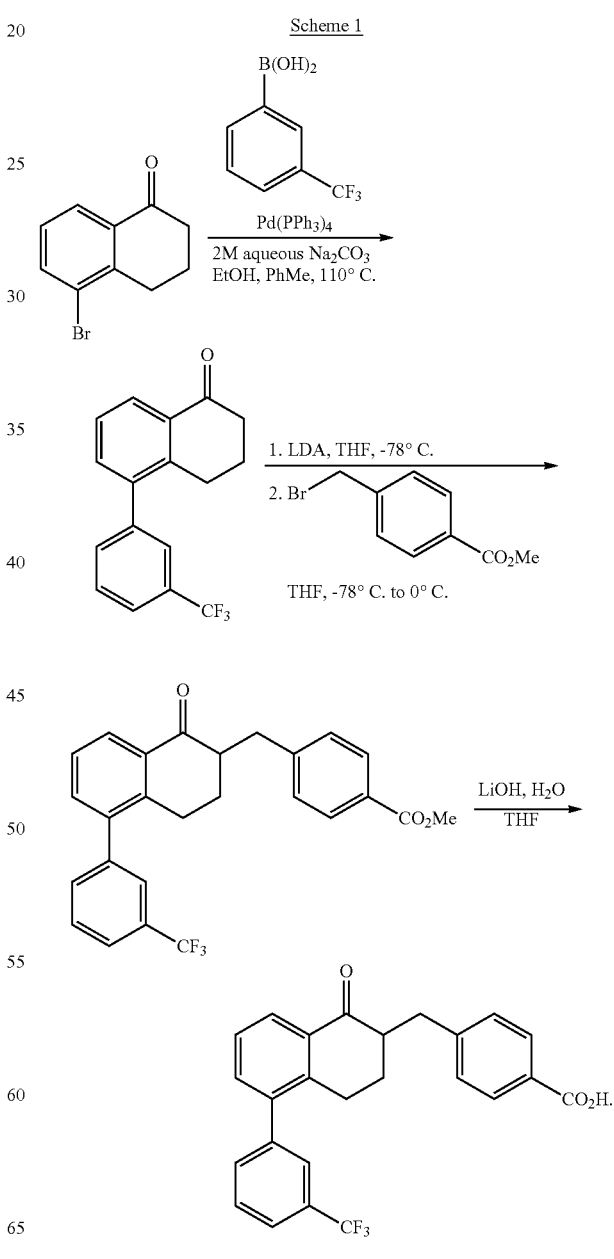

Scheme 2 sets forth below outlines a synthetic route to the compound described in Example 2:
Scheme 2
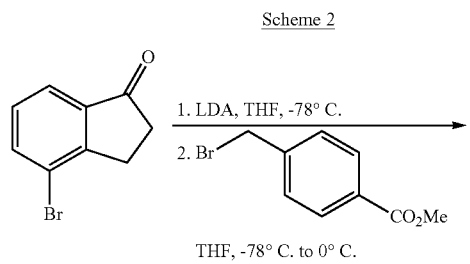
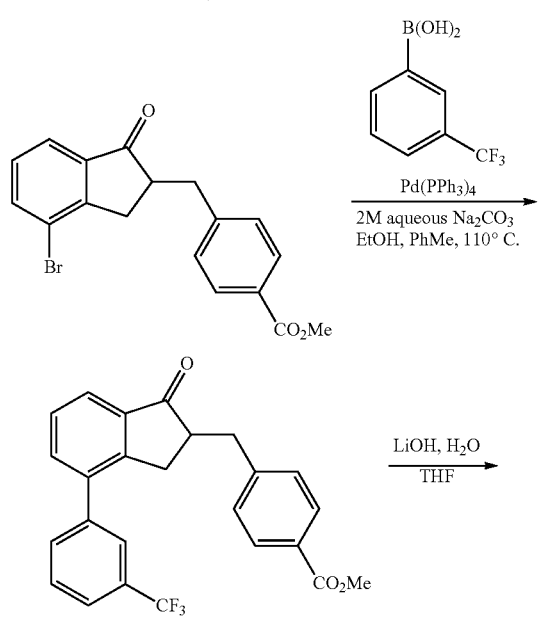
Scheme 3 sets forth a synthetic route to the compounds of the invention described in Examples 3-13:
Scheme 3
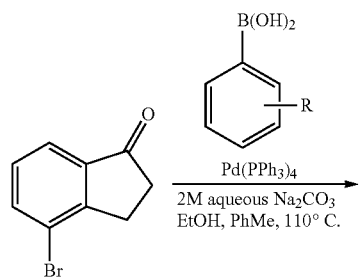
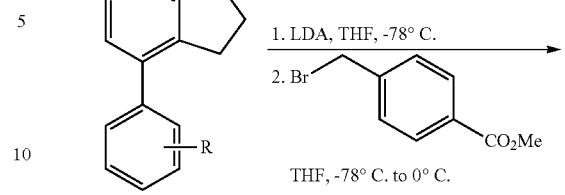
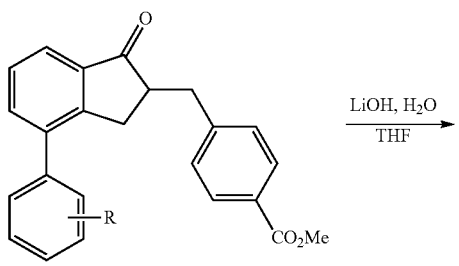
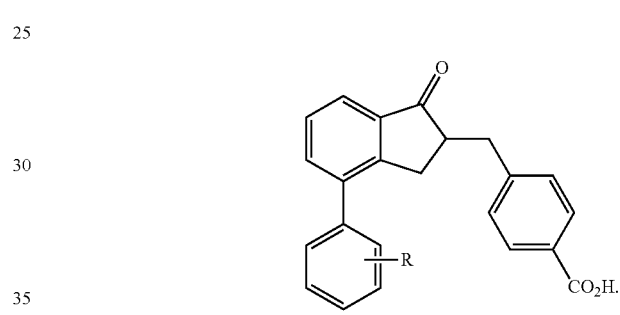
Scheme 4 sets forth a synthetic route to the compound of the invention described in Example 14:
Scheme 4
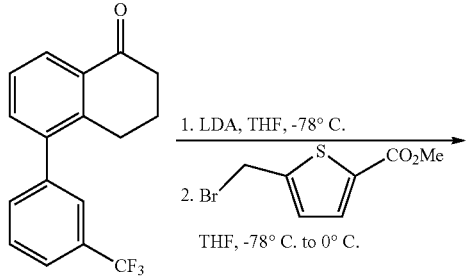
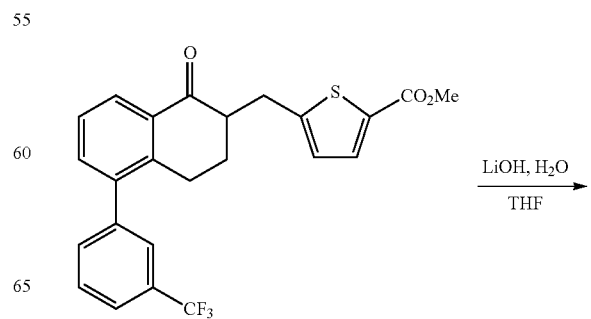

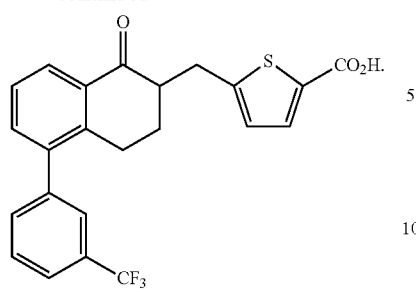
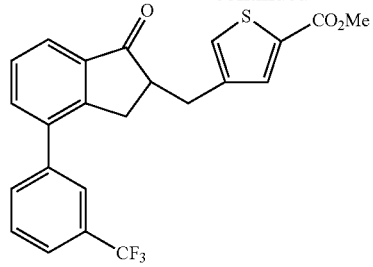
Scheme 5 sets forth a synthetic route to the compounds of the invention described in Examples 15 and 16:
Scheme 5
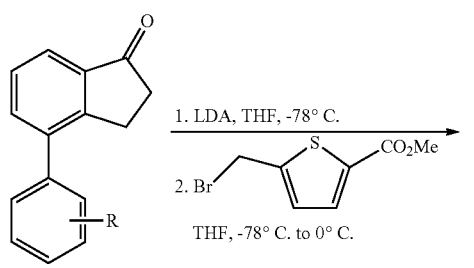
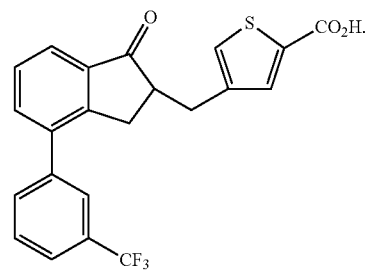
Scheme 7 sets forth a synthetic route to the compound of the invention described in Example 18:
Scheme 7
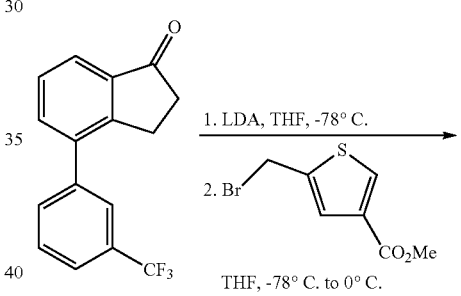
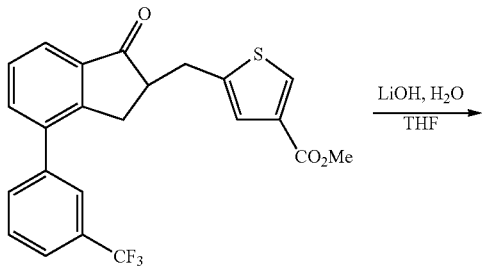
Scheme 6 sets forth a synthetic route to the compound of the invention described in Example 17:
Scheme 6
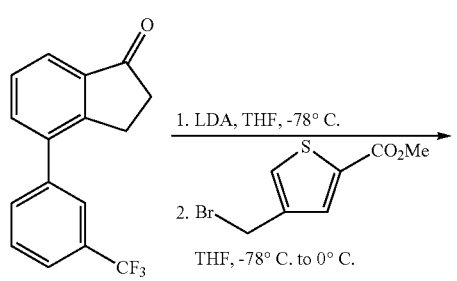
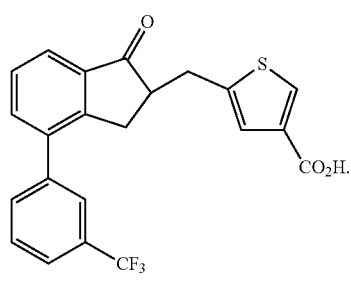

Scheme 8 sets forth a exemplary synthetic route to the compound of the invention described in Example 19:

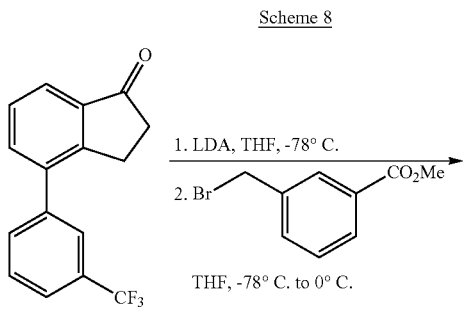

Scheme 9 sets forth a exemplary synthetic route to the compound of the invention described in Example 20:

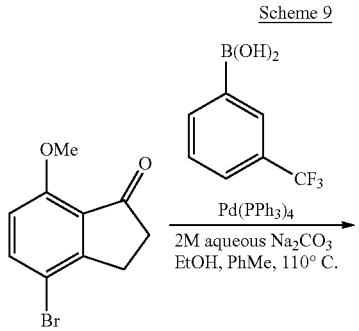

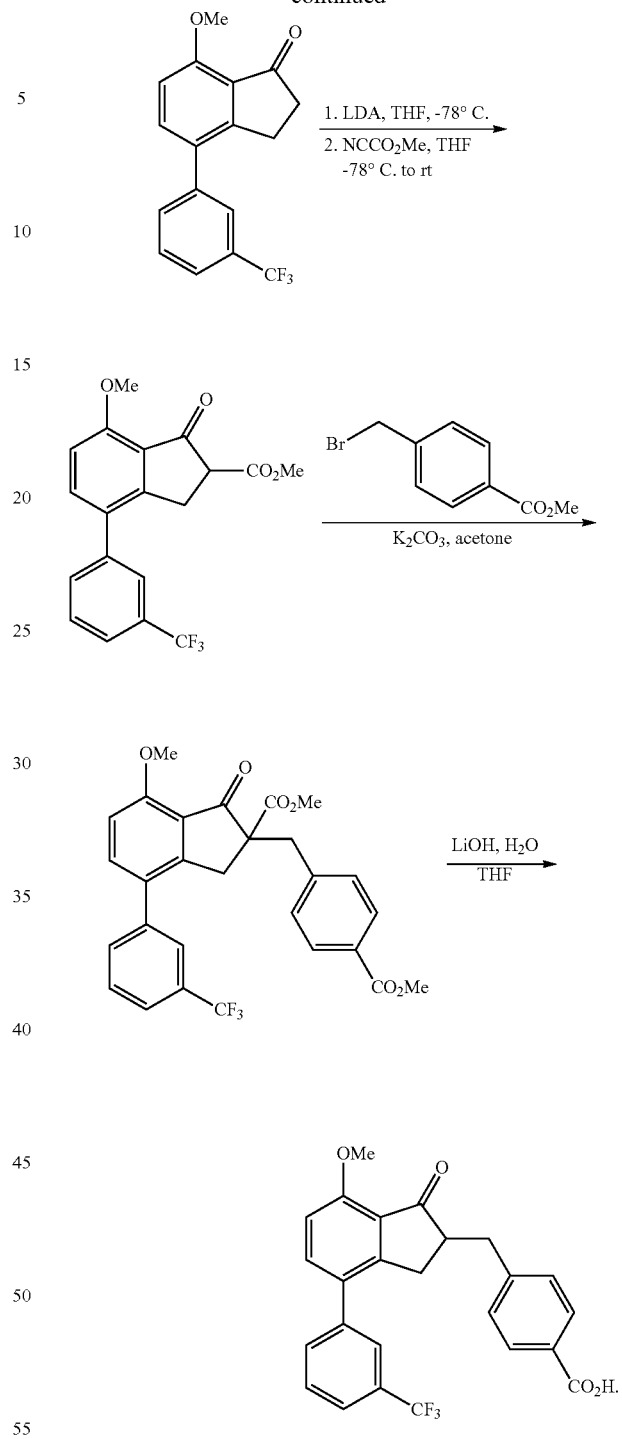

Data from running binding and activity studies on the compounds of the invention were carried out as described in U.S. Pat. No. 7,427,685, the contents of which are incorporated herein by reference. The results set forth below in Table 1 demonstrate that the compounds disclosed herein are selective prostaglandin $EP_2$ agonists, EP4 agonists, or mixed $EP_2$/$EP_4$ agonists, and are thus useful for the treatment of pathological conditions associated with $EP_2$ and/or $EP_4$ receptors.

| Example | Structure | EP2 Data (EC50 in nM) | | EP4 data (EC50 in nM) | | Other Receptors (EC50 in nM) | | | | | |
|---|---|---|---|---|---|---|---|---|---|---|---|
| | | cAMP | Ki | cAMP | KI | hFP | hEP1 | hEP3A | hTP | hIP | hDP |
| 1 | 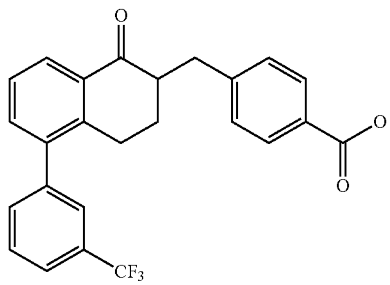 [SMILES: O=C(O)c1ccc(CC2CCc3c(cccc3-c3cccc(C(F)(F)F)c3)C2=O)cc1] | 6 | 70 | 196 | 149 | NA | NA | NA | NA | NA | NA |
| 2 | 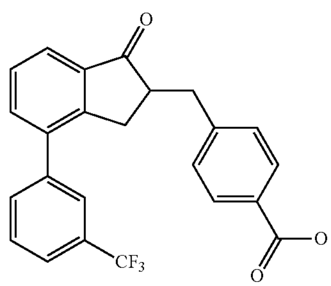 [SMILES: O=C(O)c1ccc(CC2Cc3c(cccc3-c3cccc(C(F)(F)F)c3)C2=O)cc1] | 1 | 56 | 108 | 18 | NA | NA | NA | NA | NA | NA |
| 3 | 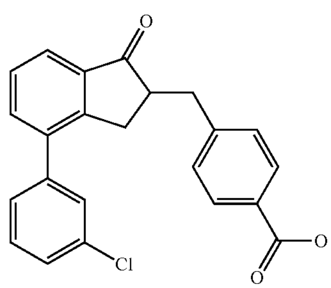 [SMILES: O=C(O)c1ccc(CC2Cc3c(cccc3-c3cccc(Cl)c3)C2=O)cc1] | 26 | 130 | 1073 | 954 | NA | NA | NA | NA | NA | NA |
| 4 | 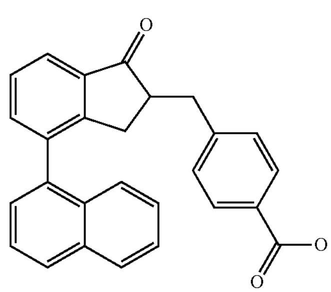 [SMILES: O=C(O)c1ccc(CC2Cc3c(cccc3-c3cccc4ccccc34)C2=O)cc1] | NT | 2080 | 1239 | 1281 | NT | NT | NT | NT | NT | NT |
| 5 | 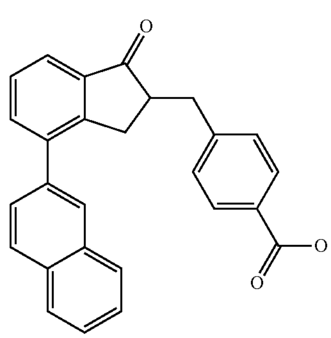 [SMILES: O=C(O)c1ccc(CC2Cc3c(cccc3-c3ccc4ccccc4c3)C2=O)cc1] | 40 | 61 | >10000 | 1192 | NT | NT | NT | NT | NT | NT |

-continued
| Example | Structure | EP2 Data (EC50 in nM) | | EP4 data (EC50 in nM) | | Other Receptors (EC50 in nM) | | | | | |
|---|---|---|---|---|---|---|---|---|---|---|---|
| | | cAMP | Ki | cAMP | KI | hFP | hEP1 | hEP3A | hTP | hIP | hDP |
| 6 | 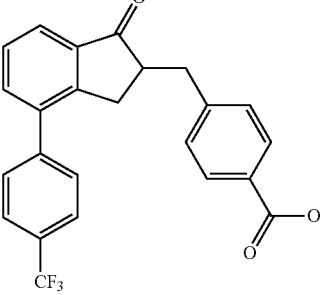 | NT | 338 | >10000 | 4446 | NT | NT | NT | NT | NT | NT |
| 7 | 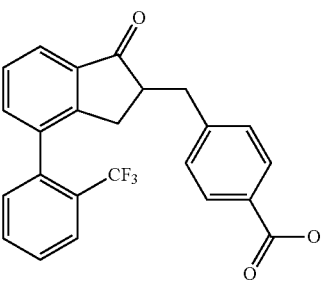 [SMILES: O=C(O)c1ccc(CC2Cc3c(cccc3-c3ccccc3C(F)(F)F)C2=O)cc1] | NT | >10000 | >10000 | 7088 | NT | NT | NT | NT | NT | NT |
| 8 | 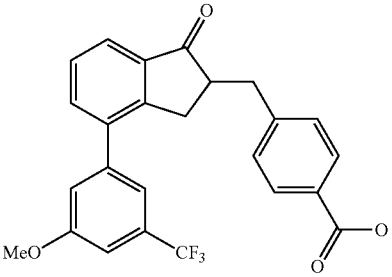 [SMILES: COc1cc(-c2cccc3c2CC(Cc2ccc(C(=O)O)cc2)C3=O)cc(C(F)(F)F)c1] | 11 | 21 | 1052 | 889 | NA | NA | NA | NA | NT | NA |
| 9 | 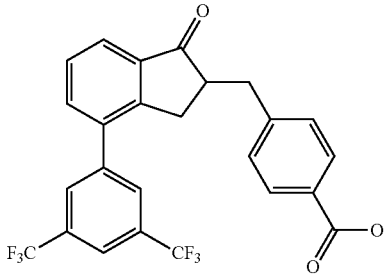 [SMILES: O=C(O)c1ccc(CC2Cc3c(cccc3-c3cc(C(F)(F)F)cc(C(F)(F)F)c3)C2=O)cc1] | 5 | 9 | 1631 | 1780 | NA | NA | NA | NA | NT | NA |
| 10 | 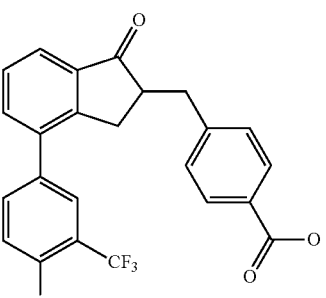 | 1 | 3 | 1088 | 1354 | NT | NT | NT | NT | NT | NT |

-continued

| Example | Structure | EP2 Data (EC50 in nM) | | EP4 data (EC50 in nM) | | Other Receptors (EC50 in nM) | | | | | |
|---|---|---|---|---|---|---|---|---|---|---|---|
| | | cAMP | Ki | cAMP | KI | hFP | hEP1 | hEP3A | hTP | hIP | hDP |
| 11 | 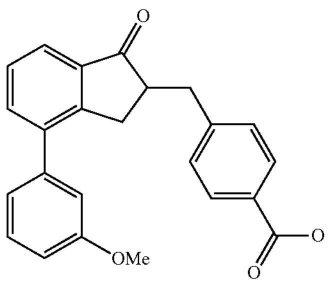 | NT | 333 | 186 | 525 | NT | NA | NT | NA | NT | NA |
| 12 | 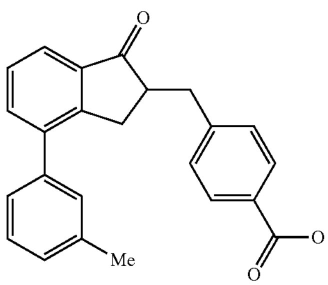 [SMILES: Cc1cccc(-c2cccc3c2CC(Cc2ccc(C(=O)O)cc2)C3=O)c1] | 217 | 191 | 1170 | 610 | NT | NT | NT | NT | NT | NT |
| 13 | 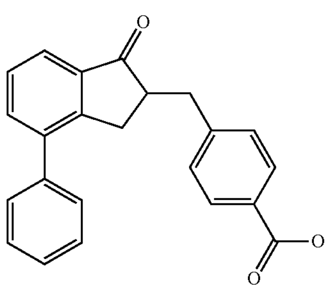 [SMILES: O=C(O)c1ccc(CC2Cc3c(cccc3-c3ccccc3)C2=O)cc1] | NT | 1144 | 2438 | 1008 | NT | NT | NT | NT | NT | NT |
| 14 | 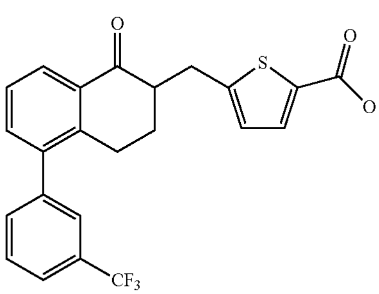 [SMILES: O=C(O)c1ccc(CC2CCc3c(cccc3-c3cccc(C(F)(F)F)c3)C2=O)s1] | 79 | 1391 | 341 | 1074 | NT | NT | NT | NT | NT | NT |
| 15 | 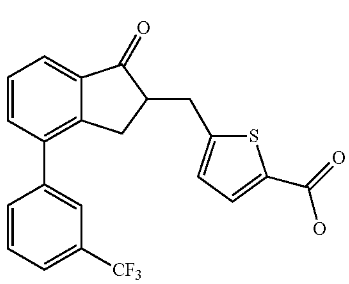 [SMILES: O=C(O)c1ccc(CC2Cc3c(cccc3-c3cccc(C(F)(F)F)c3)C2=O)s1] | 11 | 131 | 54 | 137 | NA | NA | >10000 | NA | NT | NA |

-continued

| Example | Structure | EP2 Data (EC50 in nM) | | EP4 data (EC50 in nM) | | Other Receptors (EC50 in nM) | | | | | |
|---|---|---|---|---|---|---|---|---|---|---|---|
| | | cAMP | Ki | cAMP | KI | hFP | hEP1 | hEP3A | hTP | hIP | hDP |
| 16 | 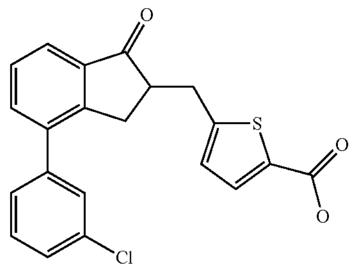 [SMILES: O=C(O)c1ccc(CC2Cc3c(cccc3-c3cccc(Cl)c3)C2=O)s1] | 62 | 199 | 300 | 505 | NA | NA | NA | NA | NT | NA |
| 17 | 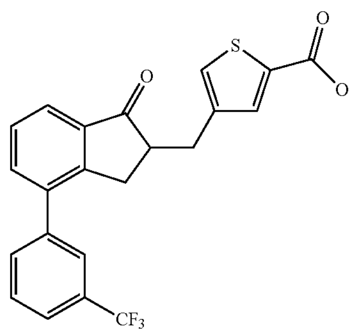 [SMILES: O=C(O)c1cc(CC2Cc3c(cccc3-c3cccc(C(F)(F)F)c3)C2=O)cs1] | 695 | 674 | >10000 | 7 | NA | NA | NA | NA | NT | NA |
| 18 | 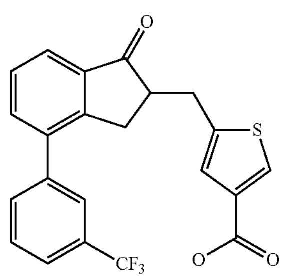 [SMILES: O=C(O)c1csc(CC2Cc3c(cccc3-c3cccc(C(F)(F)F)c3)C2=O)c1] | 179 | 96 | 4974 | 5 | NA | NA | NA | NA | NT | NA |
| 19 | 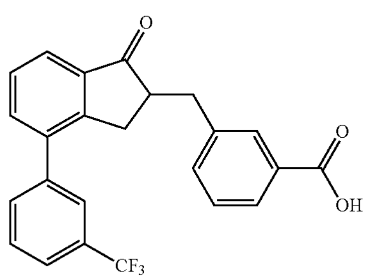 [SMILES: O=C(O)c1cccc(CC2Cc3c(cccc3-c3cccc(C(F)(F)F)c3)C2=O)c1] | NT | 6757 | 1471 | 2743 | NT | NT | NT | NT | NT | NT |
| 20 | 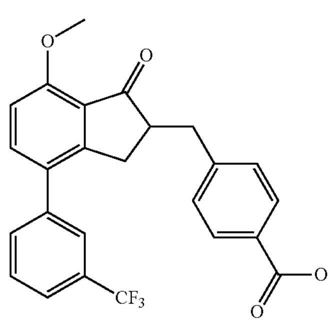 [SMILES: COc1ccc(-c2cccc(C(F)(F)F)c2)c2c1C(=O)C(Cc1ccc(C(=O)O)cc1)C2] | NT | 7355 | >10000 | 954 | NA | NA | NA | NA | NA | NA |

-continued

| Example | Structure | EP2 Data (EC50 in nM) | | EP4 data (EC50 in nM) | | Other Receptors (EC50 in nM) | | | | | |
|---|---|---|---|---|---|---|---|---|---|---|---|
| | | cAMP | Ki | cAMP | KI | hFP | hEP1 | hEP3A | hTP | hIP | hDP |
| 21 | (structure shown) | 79 | 241 | 874 | 486 | NA | NA | NA | NA | NA | NA |

Those skilled in the art will readily understand that for administration or the manufacture of medicaments the compounds disclosed herein can be admixed with pharmaceutically acceptable excipients which per se are known in the art. Specifically, a drug to be administered systemically, it may be confected as a powder, pill, tablet or the like, or as a solution, emulsion, suspension, aerosol, syrup or elixir suitable for oral or parenteral administration or inhalation.

For solid dosage forms or medicaments, non-toxic solid carriers include, but are not limited to, pharmaceutical grades of mannitol, lactose, starch, magnesium stearate, sodium saccharin, the polyalkylene glycols, talcum, cellulose, glucose, sucrose and magnesium carbonate. The solid dosage forms may be uncoated or they may be coated by known techniques to delay disintegration and absorption in the gastrointestinal tract and thereby provide a sustained action over a longer period. For example, a time delay material such as glyceryl monostearate or glyceryl distcarate may be employed. They may also be coated by the technique described in the U.S. Pat. Nos. 4,256,108; 4,166,452; and 4,265,874 to form osmotic therapeutic tablets for control release. Liquid pharmaceutically administrable dosage forms can, for example, comprise a solution or suspension of one or more of the presently useful compounds and optional pharmaceutical adjutants in a carrier, such as for example, water, saline, aqueous dextrose, glycerol, ethanol and the like, to thereby form a solution or suspension. If desired, the pharmaceutical composition to be administered may also contain minor amounts of nontoxic auxiliary substances such as wetting or emulsifying agents, pH buffering agents and the like. Typical examples of such auxiliary agents are sodium acetate, sorbitan monolaurate, triethanolamine, sodium acetate, triethanolamine oleate, etc. Actual methods of preparing such dosage forms are known, or will be apparent, to those skilled in this art; for example, see Remington's Pharmaceutical Sciences, Mack Publishing Company, Easton, Pa., 16th Edition, 1980. The composition of the formulation to be administered, in any event, contains a quantity of one or more of the presently useful compounds in an amount effective to provide the desired therapeutic effect.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol and the like. In addition, if desired, the injectable pharmaceutical compositions to be administered may also contain minor amounts of non-toxic auxiliary substances such as wetting or emulsifying agents, pH buffering agents and the like.

The amount of the presently useful compound or compounds administered is, of course, dependent on the therapeutic effect or effects desired, on the specific mammal being treated, on the severity and nature of the mammal's condition, on the manner of administration, on the potency and pharmacodynamics of the particular compound or compounds employed, and on the judgment of the prescribing physician. The therapeutically effective dosage of the presently useful compound or compounds is preferably in the range of about 0.5 or about 1 to about 100 mg/kg/day.

A liquid which is ophthalmically acceptable is formulated such that it can be administered topically to the eye. The comfort should be maximized as much as possible, although sometimes formulation considerations (e.g. drug stability) may necessitate less than optimal comfort. In the case that comfort cannot be maximized, the liquid should be formulated such that the liquid is tolerable to the patient for topical ophthalmic use. Additionally, an ophthalmically acceptable liquid should either be packaged for single use, or contain a preservative to prevent contamination over multiple uses.

For ophthalmic application, solutions or medicaments are often prepared using a physiological saline solution as a major vehicle. Ophthalmic solutions should preferably be maintained at a comfortable pH with an appropriate buffer system. The formulations may also contain conventional, pharmaceutically acceptable preservatives, stabilizers and surfactants.

Preservatives that may be used in the pharmaceutical compositions of the present invention include, but are not limited to, benzalkonium chloride, chlorobutanol, thimerosal, phenylmercuric acetate and phenylmercuric nitrate. A useful surfactant is, for example, Tween 80. Likewise, various useful vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. A useful chelating agent is edetate disodium, although other chelating agents may also be used in place or in conjunction with it.

The ingredients are usually used in the following amounts:

| Ingredient | Amount (% w/v) |
| --- | --- |
| active ingredient | about 0.001-5 |
| preservative | 0-0.10 |
| vehicle | 0-40 |
| tonicity adjustor | 1-10 |
| buffer | 0.01-10 |
| pH adjustor | q.s. pH 4.5-7.5 |
| antioxidant | as needed |
| surfactant | as needed |
| purified water | as needed to make 100% |

For topical use, creams, ointments, gels, solutions or suspensions, etc., containing the compound disclosed herein are employed. Topical formulations may generally be comprised of a pharmaceutical carrier, cosolvent, emulsifier, penetration enhancer, preservative system, and emollient.

The invention provides compositions and methods for wound healing and scar reduction. The compositions and methods of the invention include at least one EP2 agonist, at least one EP4 agonist, and/or at least one mixed $EP_2/EP_4$ agonist, as set forth herein. Wounds and or scars that can be treated by the compositions and methods of the invention can arise from events such as surgery, trauma, disease, mechanical injury, burn, radiation, poisoning, and the like.

As used herein, the term "skin blemish" includes a flesh wound, scar, or wrinkle on any region of the skin of a body.

A "flesh wound" can be any area in which the structural integrity of the exterior surface of the skin is compromised. A flesh wound can be due to incision, laceration, abrasion, thermal burn, chemical burn, radiation or puncture of the skin. The wound can be superficial or extend to the deeper layers of the dermis, subcutaneous, deep fascia, muscle, bone or other internal organs.

A "scar" is an area of fibrous tissue (fibrosis) that replaces normal skin (or other tissue) after injury or disease. Scar types include hypertrophic scars, recessed scars, and stretch marks. Hypertrophic scars occur when the body overproduces collagen, which causes the scar to be raised above the surrounding skin. An example of a hypertrophic scar is a keloid scar. Atrophic, or recessed scars, have a sunken appearance and result when underlying support structure in the skin is lost. Stretch marks (striae) occur when skin is stretched rapidly (i.e., due to significant weight gain or growth spurt), or when skin is put under tension during the healing process, typically near a joint. As used herein, the term "scar" encompasses any type of scar in the skin due to any cause.

As used herein, the term "wrinkle" is a fold, ridge, crease, furrow, pit, crater, or sunken area in the skin that can be caused by habitual facial expressions, loss of collagen and/or elasticity due to aging, sun damage, smoking, poor hydration, and various other factors. A wrinkle can range from a deep crease to a fine line. Wrinkles occurring on any part of a body, in particular, wrinkles on head or neck of a subject are contemplated herein. Wrinkles that can be treated in accordance with the disclosure include, but are not limited to, a brow furrow, crows feet, nasolabial fold, one or more lines under the eyes or between the eye brows, and combinations thereof.

As used herein, "treatment" means to alleviate (or to eliminate) one or more features of a skin blemish either temporarily or permanently. When the compositions are administered to treat a wound, the compositions promote normal healing compared to a wound without the administration. That is, the size (length, depth, height and/or width), character, color and/or texture of the treated wound more closely resemble normal, non-wounded tissue. In this regard, treatment of a wound with the disclosed compositions can prevent, minimize or improve the appearance of a scar formation resulting from healing of the wound. Further, when the disclosed compositions are administered to treat a wrinkle, the wrinkle is treated if the appearance or prominence of the wrinkle is visibly or clinically diminished. That is the length and/or depth is decreased compared to the wrinkle prior to treatment. Alternatively, treatment can comprise prevention of a wrinkle. In this regard, the disclosed compositions can be applied to a region of the skin that typically develops a wrinkle, such as a forehead, lips, eyelids, nasolabial fold, skin under an eye, or between the eye brows in order to prevent the development of a wrinkle.

The disclosed compositions can be administered to prevent scar formation not associated with a wound, such as a stretch mark, or scars resulting from acne, chicken pox, measles or other disease states. In certain embodiments, the disclosed compositions are administered to the area of skin expansion in order to prevent formation of such scars. In these embodiments, the composition can be administered to any region of a face, abdomen, breasts, arms, legs, buttocks, back, or any other area where the skin is susceptible to developing a scar.

The compositions can be administered prior to, concurrently with, and/or after the development of the skin blemish. For instance, the disclosed compositions can be administered prior to an incision, during a surgical procedure, and/or any time post-operatively, and then additionally administered after the procedure as the healing process occurs. In another example, the compositions can be administered during pregnancy to prevent stretch marks. Alternately, the compositions can be administered after the development of a blemish.

The compositions may be administered between 1 and 7 days a week, for a period of time necessary to achieve the desired results, which may be several days to several months. The compositions can be administered once or several times (2, 3, 4, or more times) a day depending on the desired effect. In certain embodiments, the compositions can be administered every 1, 2, 3, 4, 5, 6, or 7 days. In another embodiment, the compositions can be administered one or more times every 1, 2, 3, or 4 weeks. The administration can be on a monthly or bi-monthly basis. Further, the compositions can be administered for 1, 2, 3, 6, 9, or 12 months or more. In certain embodiments, the compositions can be administered on an ongoing basis to maintain a desired result.

The disclosed compounds can be administered as part of a composition. As used herein, "formulation" and "composition" may be used interchangeably and refer to a combination of elements that is presented together for a given purpose. Such terms are well known to those of ordinary skill in the art.

As used herein, "carrier," "inert carrier," and "acceptable carrier" may be used interchangeably and refer to a carrier which may be combined with the presently disclosed compounds in order to provide a desired composition. Those of ordinary skill in the art will recognize a number of carriers that are well known for making specific pharmaceutical and/or cosmetic compositions. Desirably, the carrier is suitable for application to keratinous surfaces or other areas of the body. Upon application, acceptable carriers are substantially free of adverse reactions with skin and other keratinous surfaces. For example, the carriers may take the form of fatty or non-fatty creams, milky suspensions or emulsion-in-oil or oil-in-water types, lotions, gels or jellies, colloidal or non-colloidal aqueous or oily solutions, pastes, aerosols, soluble tablets or sticks. In accordance with one embodiment, the composition includes a dermatologically compatible vehicle or carrier. The vehicle which may be employed for preparing compositions may comprise, for example, aqueous solutions such as e.g., physiological salines, oil solutions or ointments. The vehicle furthermore may contain dermatologically compatible preservatives such as e.g., benzalkonium chloride, surfactants like e.g., polysorbate 80, liposomes or polymers, for example, methyl cellulose, polyvinyl alcohol, polyvinyl pyrrolidone and hyaluronic acid; these may be used for increasing the viscosity.

Examples of additional agents which can be included in the present compositions are anti-itch, anti-cellulite, anti-scarring, and anti-inflammatory agents, anesthetics, anti-irritants, vasoconstrictors, vasodilators, as well as agents to prevent/stop bleeding, and improve/remove pigmentation, moisturizers, desquamating agents, tensioning agents, anti-acne agents. Anti-itch agents can include methyl sulphonyl methane, sodium bicarbonate, calamine, allantoin, kaolin, peppermint, tea tree oil and combinations thereof. Anti-cellulite agents can include forskolin, xanthine compounds such as, but not limited to, caffeine, theophylline, theobromine, and aminophylline, and combinations thereof. Anesthetic agents can include lidocaine, benzocaine, butamben, dibucaine, oxybuprocaine, pramoxine, proparacaine, proxymetacaine, tetracaine, and combinations thereof. Anti-scarring agents can include IFN-.gamma., fluorouracil, poly(lactic-co-glycolic acid), methylated polyethylene glycol, polylactic acid, polyethylene glycol and combinations thereof. Anti-inflammatory agents can include dexamethasone, prednisolone, corticosterone, budesonide, estrogen, sulfasalazine, mesalamine and derivatives and combinations thereof. Additionally, active agents such as epinephrine, thymidine, cytidine, uridine, antiypyrin, aminocaproic acid, tranexamic acid, eucalyptol, allantoin, glycerin, and sodium selenite, can be included. Formulations can further comprise degradation inhibitors. Degradation inhibitors, include but are not limited to, glycosaminoglycans (e.g., heparin, heparin sulfate, dermatan sulfate, chrondroitin sulfate, o-sulfated HA, lnamarin, and amygdalin), antioxidants (e.g. ascorbic acid, melatonin, vitamin C, vitamin E), proteins (e.g., serum hyaluronidase inhibitor), and fatty acids (e.g. saturated $C_{10}$ to $C_{22}$ fatty acids). In certain embodiments, additional active agent is an antioxidant. In certain embodiments, the antioxidant comprises a vitamin C and/or a vitamin E such as d-alpha-tocopheryl polyethylene glycol 1000 succinate (TPGS).

The disclosed compositions are well suited for topical, subcutaneous, intradermal, subdermal, subcutaneous, and trandermal administration. Topical administration relates to the use of a composition applied to the surface of the skin at the site of a skin blemish for exertion of local action. Accordingly, such topical compositions include those pharmaceutical or cosmetic forms in which the composition is applied externally by direct contact with the skin surface to be treated, such as the face, neck, arms, legs, and/or torso. Conventional pharmaceutical or cosmetic forms for this purpose include ointments, liniments, creams, shampoos, lotions, pastes, jellies, sprays, aerosols, and the like, and may further be applied directly or in patches or impregnated dressings depending on blemish and skin region to be treated. The term "ointment" embraces formulations (including creams) having oleaginous, water-soluble and emulsion-type bases, e.g., petrolatum, lanolin, polyethylene glycols, as well as mixtures of these.

The compositions are appropriate for mesotherapy applications as well. Mesotherapy is a non-surgical cosmetic treatment technique involving intra-epidermal, intra-dermal, and/or subcutaneous injection of a composition. The compositions are administered in the form of small multiple droplets into the epidermis, dermo-epidermal junction, and/or the dermis.

The actual dose of the active compounds of the present invention depends on the specific compound, and on the condition to be treated; the selection of the appropriate dose is well within the knowledge of the skilled artisan.

The compounds disclosed herein are also useful in combination with other drugs useful for the treatment of glaucoma or other conditions.

For the treatment of glaucoma, combination treatment with the following classes of drugs are contemplated:

β-Blockers (or β-adrenergic antagonists) including carteolol, levobunolol, metiparanolol, timolol hemihydrate, timolol maleate, β1-selective antagonists such as betaxolol, and the like, or pharmaceutically acceptable salts or prodrugs thereof;

Adrenergic Agonists including non-selective adrenergic agonists such as epinephrine borate, epinephrine hydrochloride, and dipivefrin, and the like, or pharmaceutically acceptable salts or prodrugs thereof; and $α_2$-selective adrenergic agonists such as apraclonidine, brimonidine, and the like, or pharmaceutically acceptable salts or prodrugs thereof;

Carbonic Anhydrase Inhibitors including acetazolamide, dichlorphenamide, methazolamide, brinzolamide, dorzolamide, and the like, or pharmaceutically acceptable salts or prodrugs thereof;

Cholinergic Agonists including direct acting cholinergic agonists such as carbachol, pilocarpine hydrochloride, pilocarbine nitrate, pilocarpine, and the like, or pharmaceutically acceptable salts or prodrugs thereof;

chlolinesterase inhibitors such as demecarium, echothiophate, physostigmine, and the like, or pharmaceutically acceptable salts or prodrugs thereof;

Glutamate Antagonists and other neuroprotective agents such as $Ca^+$ channel blockers such as memantine, amantadine, rimantadine, nitroglycerin, dextrophan, dextromethorphan, CGS-19755, dihydropyridines, verapamil, emopamil, benzothiazepines, bepridil, diphenylbutylpiperidines, diphenylpiperazines, HOE 166 and related drugs, fluspirilene, eliprodil, ifenprodil, CP-101,606, tibalosine, 2309BT, and 840S, flunarizine, nicardipine, nifedimpine, nimodipine, barnidipine, verapamil, lidoflazine, prenylamine lactate, amiloride, and the like, or pharmaceutically acceptable salts or prodrugs thereof;

Prostamides such as bimatoprost, or pharmaceutically acceptable salts or prodrugs thereof; and Prostaglandins including travoprost, UFO-21, chlorostenol, fluprostenol, 13,14-dihydro-chloprostenol, isopropyl unoprostone, latanoprost and the like.

Cannabinoids including CB1 agonists such as WIN-55212-2 and CP-55940 and the like, or pharmaceutically acceptable salts or prodrugs thereof.

For treatment of diseases affecting the eye including glaucoma, these compounds can be administered topically, periocularly, intraocularly, or by any other effective means known in the art.

Pathological conditions associated with EP2 and/or EP4 receptors include, but are not limited to, acute hepatitis, asthma, bronchitis, burn, chronic obstructive respiratory diseases, Crohn's disease, digestive ulcer, glaucoma (and other diseases related to elevated intraocular pressure), hemophagous syndrome, hepatopathy, hypercytokinemia at dialysis, hypertension, immunological diseases (autoimmune diseases, organ transplantation, etc.), inflammation (such as rheumatoid arthritis), Kawasaki disease, liver injury, macrophage activation syndrome, myocardial ischemia, nephritis, nerve cell death, osteoporosis and diseases associated with bone disorders, premature birth, pulmonary emphysema, pulmonary fibrosis, pulmonary injury, renal failure, sepsis, sexual dysfunction, shock, sleep disorder, Still disease, stomatitis, systemic granuloma, systemic inflammatory syndrome, thrombosis and stroke, and ulcerative colitis.

The following examples are intended only to illustrate the invention and should in no way be construed as limiting the invention.

EXAMPLES

Example 1

4-((1-Oxo-5-(3-(trifluoromethyl)phenyl)-1,2,3,4-tetrahydronaphthalen-2-yl)methyl)benzoic acid Step 1. 5-(3-(Trifluoromethyl)phenyl)-3,4-dihydronaphthalen-1(2H)-one A 50 mL Schlenk tube was charged with 5-bromo-3,4-dihydronaphthalen-1(2H)-one (5-bromo-1-tetralone [Aldrich], 488 mg, 2.17 mmol), which was dissolved in toluene (2.5 mL) under a nitrogen atmosphere. Tetrakis(triphenylphosphine) palladium (0) (70 mg, 0.06 mmol) was added to the flask followed by more toluene (2.5 mL). Aqueous sodium carbonate (2.0 M, 2 mL, 4 mmol) was added, followed by a solution of 3-trifluoromethylphenyl boronic acid (489 mg, 2.57 mmol) in ethanol (2.5 mL). A nitrogen atmosphere was established by evacuating and refilling with nitrogen (3×), then the flask was sealed and heated in a 110° C. oil bath overnight. The resulting mixture was cooled to room temperature. Aqueous hydrogen peroxide solution (30%, 0.3 mL) was added and the mixture was stirred for 1 h. The reaction was then diluted with water (25 mL) and extracted with ethyl ether or EtOAc (3×75 mL). The combined organic extracts were dried (Na$_2$SO$_4$), filtered and concentrated. The resulting crude residue was purified on a Teledyne-Isco Combiflash machine (40 g column, hexanes→40% EtOAc/hexanes, gradient), to afford 628 mg (99%) of 5-(3-(trifluoromethyl)phenyl)-3,4-dihydronaphthalen-1(2H)-one.

Step 2. Methyl 4-((1-oxo-5-(3-(trifluoromethyl)phenyl)-1,2,3,4-tetrahydronaphthalen-2-yl)methyl)benzoate A solution of lithium diisopropylamide (2.0 M in THF, 0.8 mL, 1.6 mmol) was added to a solution of 5-(3-(trifluoromethyl)phenyl)-3,4-dihydronaphthalen-1(2H)-one (435 mg, 1.5 mmol) in THF (5 mL) at −78° C. After 1 h at −78° C., a solution of methyl 4-(bromomethyl)benzoate (378 mg, 1.65 mmol) in THF (2.5 mL) was added via cannula. The reaction mixture was allowed to warm to room temperature naturally. After stirring at room temperature overnight, the reaction was quenched with saturated aqueous NH$_4$Cl (25 mL) and extracted with EtOAc (3×50 mL). The combined organic extracts were dried (Na$_2$SO$_4$), filtered and concentrated. The resulting crude residue was purified by combiflash (40 g column, hexanes→40% EtOAc/hexanes, gradient) to afford 55 mg (8%) of methyl 4-((1-oxo-5-(3-(trifluoromethyl)phenyl)-1,2,3,4-tetrahydronaphthalen-2-yl)methyl)benzoate.

Step 3. 4-((1-oxo-5-(3-(trifluoromethyl)phenyl)-1,2,3,4-tetrahydronaphthalen-2-yl)methyl)benzoic acid Aqueous lithium hydroxide (1 N, 0.11 mL, 0.11 mmol) was added to a solution of methyl4-((1-oxo-5-(3-(trifluoromethyl)phenyl)-1,2,3,4-tetrahydronaphthalen-2-yl)methyl)benzoate (10 mg, 0.023 mmol) in THF (0.23 mL) in a 1 dram vial. The vial was sealed and heated at 40° C. After 24 h, the reaction mixture was allowed to cool and the volatiles were evaporated under a stream of nitrogen. The residue was diluted with water (0.5 mL), acidified with 1 N aqueous HCl (0.5 mL) and extracted with EtOAc (3×2 mL). The combined organic extracts were dried (Na$_2$SO$_4$), filtered and concentrated in vacuo to afford 9 mg of the title compound.

Example 2

4-((1-Oxo-4-(3-(trifluoromethyl)phenyl)-2,3-dihydro-1H-inden-2-yl)methyl)benzoic acid Step 1. Methyl 4-((4-bromo-1-oxo-2,3-dihydro-1H-inden-2-yl)methyl)benzoate A solution of lithium diisopropylamide (2.0 M in THF, 2.5 mL, 5.0 mmol) was added to a solution of 4-bromo-2,3-dihydro-1H-inden-1-one (4-bromo-1-indanone, 960 mg, 4.55 mmol) in THF (9.1 mL) at −78° C. After 1 h at −78° C., a solution of methyl 4-(bromomethyl)benzoate (1.25 g, 5.46 mmol) in THF (5 mL) was added via cannula. The reaction mixture was allowed to warm to room temperature naturally. After stirring at room temperature overnight, the reaction was quenched with saturated aqueous NH$_4$Cl (50 mL) and extracted with EtOAc (3×100 mL). The combined organic extracts were dried (Na$_2$SO$_4$), filtered and concentrated. The resulting crude residue was purified by combiflash (330 g column, hexanes→30% EtOAc/hexanes, gradient) to afford 72 mg (4%) of methyl 4-((4-bromo-1-oxo-2,3-dihydro-1H-inden-2-yl)methyl)benzoate.

Step 2. Methyl 4-((1-oxo-4-(3-(trifluoromethyl)phenyl)-2,3-dihydro-1H-inden-2-yl)methyl)benzoate In accordance with the procedure of Example 1, step 1, methyl 4-((4-bromo-1-oxo-2,3-dihydro-1H-inden-2-yl)methyl)benzoate (72 mg, 0.20 mmol) and 3-trifluoromethylphenyl boronic acid (45 mg, 0.24 mmol) were converted into 82 mg (96%) of methyl 4-((1-oxo-4-(3-(trifluoromethyl)phenyl)-2,3-dihydro-1H-inden-2-yl)methyl)benzoate after combiflash purification (12 g column, hexanes→40% EtOAc/hexanes, gradient).

Step 3. 4-((1-Oxo-4-(3-(trifluoromethyl)phenyl)-2,3-dihydro-1H-inden-2-yl)methyl)benzoic acid In accordance with the procedure of Example 1, step 3, methyl 4-((1-oxo-4-(3-(trifluoromethyl)phenyl)-2,3-dihydro-1H-inden-2-yl)methyl)benzoate (13 mg, 0.031 mmol) was converted into 10 mg (79%) of the title compound.

Example 3

4-((4-(3-Chlorophenyl)-1-oxo-2,3-dihydro-1H-inden-2-yl)methyl)benzoic acid

Step 1. 4-(3-Chlorophenyl)-2,3-dihydro-1H-inden-1-one

In accordance with Example 1, step 1, 4-bromo-2,3-dihydro-1H-inden-1-one (4-bromo-1-indanone, 211 mg, 1.0 mmol) and 3-chlorophenyl boronic acid (188 mg, 1.2 mmol) were converted into 235 mg (97%) of 4-(3-chlorophenyl)-2,3-dihydro-1H-inden-1-one after combiflash purification (40 g column, hexanes→35% EtOAc/hexanes, gradient).

Step 2. Methyl 4-((4-(3-chlorophenyl)-1-oxo-2,3-dihydro-1H-inden-2-yl)methyl)benzoate A solution of lithium diisopropylamide (2.0 M in THF, 0.49 mL, 0.98 mmol) was added to a solution of 4-(3-chlorophenyl)-2,3-dihydro-1H-inden-1-one (235 mg, 0.97 mmol) in THF (3.3 mL) at −78° C. After 1 h at −78° C., a solution of methyl 4-(bromomethyl)benzoate (229 mg, 1.0 mmol) in THF (1.7 mL) was added via cannula. After 1 h at −78° C., the mixture was allowed to slowly warm to 0° C. After 1 h at 0° C., the reaction was quenched with saturated aqueous NH$_4$Cl (50 mL) and extracted with EtOAc (3×50 mL). The combined organic extracts were dried (Na$_2$SO$_4$), filtered and concentrated. The resulting crude residue was purified by combiflash (40 g column, hexanes→30% EtOAc/hexanes, gradient) to afford 20 mg (5%) of methyl 4-((4-(3-chlorophenyl)-1-oxo-2,3-dihydro-1H-inden-2-yl)methyl)benzoate.

Step 3. 4-((4-(3-Chlorophenyl)-1-oxo-2,3-dihydro-1H-inden-2-yl)methyl)benzoic acid In accordance with the procedure of Example 1, step 3, methyl 4-((4-(3-chlorophenyl)-1-oxo-2,3-dihydro-1H-inden-2-yl)methyl)benzoate (10 mg, 0.026 mmol) was converted into 9 mg (92%) of the title compound.

Example 4

4-((4-(Naphthalen-1-yl)-1-oxo-2,3-dihydro-1H-inden-2-yl)methyl)benzoic acid Step 1. 4-(Naphthalen-1-yl)-2,3-dihydro-1H-inden-1-one In accordance with the procedure of Example 1, step 1, 4-bromo-2,3-dihydro-1H-inden-1-one (4-bromo-1-indanone, 211 mg, 1.0 mmol) and naphthalene-1-boronic acid (205 mg, 1.2 mmol) were converted into 254 mg (98%) of 4-(naphthalen-1-yl)-2,3-dihydro-1H-inden-1-one after combiflash purification (40 g column, hexanes→35% EtOAc/hexanes, gradient).

Step 2. Methyl 4-((4-(naphthalen-1-yl)-1-oxo-2,3-dihydro-1H-inden-2-yl)methyl)benzoate A solution of lithium diisopropylamide (2.0 M in THF, 0.50 mL, 1.0 mmol) was added to a solution of 4-(naphthalen-1-yl)-2,3-dihydro-1H-inden-1-one (254 mg, 0.98 mmol) in THF (3.4 mL) at −78° C. After 1 h at −78° C., a solution of methyl 4-(bromomethyl)benzoate (230 mg, 1.0 mmol) in THF (1.7 mL) was added via cannula. After 1 h at −78° C., the mixture was allowed to slowly warm to 0° C. After 30 min at 0° C., the reaction was quenched with saturated aqueous NH$_4$Cl (25 mL), diluted with water (10 mL) and extracted with EtOAc (3×50 mL). The combined organic extracts were dried (Na$_2$SO$_4$), filtered and concentrated. The resulting crude residue was purified by combiflash (40 g column, hexanes→30% EtOAc/hexanes, gradient) to afford 53 mg (13%) of methyl 4-((4-(naphthalen-1-yl)-1-oxo-2,3-dihydro-1H-inden-2-yl)methyl)benzoate.

Step 3. 4-((4-(Naphthalen-1-yl)-1-oxo-2,3-dihydro-1H-inden-2-yl)methyl)benzoic acid In accordance with the procedure of Example 1, step 3, methyl 4-((4-(naphthalen-1-yl)-1-oxo-2,3-dihydro-1H-inden-2-yl)methyl)benzoate (13 mg, 0.032 mmol) was converted into 12 mg (96%) of the title compound.

Example 5

4-((4-(Naphthalen-2-yl)-1-oxo-2,3-dihydro-1H-inden-2-yl)methyl)benzoic acid Step 1. 4-(Naphthalen-2-yl)-2,3-dihydro-1H-inden-1-one In accordance with the procedure of Example 1, step 1, 4-bromo-2,3-dihydro-1H-inden-1-one (4-bromo-1-indanone, 211 mg, 1.0 mmol) and 2-naphthylboronic acid (205 mg, 1.2 mmol) were converted into 255 mg (98%) of 4-(naphthalen-2-yl)-2,3-dihydro-1H-inden-1-one after combiflash purification (40 g column, hexanes→30% EtOAc/hexanes, gradient).

Step 2. Methyl 4-((4-(naphthalen-2-yl)-1-oxo-2,3-dihydro-1H-inden-2-yl)methyl)benzoate In accordance with the procedure of Example 4, step 2, 4-(naphthalen-2-yl)-2,3-dihydro-1H-inden-1-one (255 mg, 0.98 mmol) and methyl 4-(bromomethyl)benzoate (230 mg, 1.0 mmol) were converted into 65 mg (16%) of methyl 4-((4-(naphthalen-2-yl)-1-oxo-2,3-dihydro-1H-inden-2-yl)methyl)benzoate after combiflash purification (40 g column, hexanes→25% EtOAc/hexanes, gradient).

Step 3. 4-((4-(Naphthalen-2-yl)-1-oxo-2,3-dihydro-1H-inden-2-yl)methyl)benzoic acid In accordance with the procedure of Example 1, step 3, methyl 4-((4-(naphthalen-2-yl)-1-oxo-2,3-dihydro-1H-inden-2-yl)methyl)benzoate (12 mg, 0.030 mmol) was converted into 9 mg (78%) of the title compound.

Example 6

4-β1-oxo-4-(4-(trifluoromethyl)phenyl)-2,3-dihydro-1H-inden-2-yl)methyl)benzoic acid Step 1. 4-(4-(Trifluoromethyl)phenyl)-2,3-dihydro-1H-inden-1-one In accordance with the procedure of Example 1, step 1, 4-bromo-2,3-dihydro-1H-inden-1-one (4-bromo-1-indanone, 211 mg, 1.0 mmol) and 4-trifluoromethylphenyl boronic acid (228 mg, 1.2 mmol) were converted into 275 mg (99%) of 4-(4-(trifluoromethyl)phenyl)-2,3-dihydro-1H-inden-1-one after combiflash purification (40 g column, hexanes→25% EtOAc/hexanes, gradient).

Step 2. Methyl 4-((1-oxo-4-(4-(trifluoromethyl)phenyl)-2,3-dihydro-1H-inden-2-yl)methyl)benzoate In accordance with the procedure of Example 4, step 2, 4-(4-(trifluoromethyl)phenyl)-2,3-dihydro-1H-inden-1-one (275 mg, 0.99 mmol) and methyl 4-(bromomethyl)benzoate (235 mg, 1.03 mmol) were converted into 100 mg (24%) of methyl 4-((1-oxo-4-(4-(trifluoromethyl)phenyl)-2,3-dihydro-1H-inden-2-yl)methyl)benzoate after combiflash purification (40 g column, hexanes→30% EtOAc/hexanes, gradient).

Step 3. 4-((1-Oxo-4-(4-(trifluoromethyl)phenyl)-2,3-dihydro-1H-inden-2-yl)methyl)benzoic acid In accordance with the procedure of Example 1, step 3, methyl 4-((1-oxo-4-(4-(trifluoromethyl)phenyl)-2,3-dihydro-1H-inden-2-yl)methyl)benzoate (9 mg, 0.021 mmol) was converted into 7 mg (80%) of the title compound.

Example 7

4-((1-Oxo-4-(2-(trifluoromethyl)phenyl)-2,3-dihydro-1H-inden-2-yl)methyl)benzoic acid Step 1. 4-(2-(Trifluoromethyl)phenyl)-2,3-dihydro-1H-inden-1-one In accordance with the procedure of Example 1, step 1, 4-bromo-2,3-dihydro-1H-inden-1-one (4-bromo-1-indanone, 211 mg, 1.0 mmol) and 2-trifluoromethylphenyl boronic acid (228 mg, 1.2 mmol) were converted into 267 mg (97%) of 4-(2-(trifluoromethyl)phenyl)-2,3-dihydro-1H-inden-1-one after combiflash purification (40 g column, hexanes→30% EtOAc/hexanes, gradient).

Step 2. Methyl 4-((1-oxo-4-(2-(trifluoromethyl)phenyl)-2,3-dihydro-1H-inden-2-yl)methyl)benzoate In accordance with the procedure of Example 4, step 2, 4-(2-(trifluoromethyl)phenyl)-2,3-dihydro-1H-inden-1-one (267 mg, 0.97 mmol) and methyl 4-(bromomethyl)benzoate (230 mg, 1.0 mmol) were converted into 80 mg (20%) of methyl 4-((1-oxo-4-(2-(trifluoromethyl)phenyl)-2,3-dihydro-1H-inden-2-yl)methyl)benzoate after combiflash purification (40 g column, hexanes→25% EtOAc/hexanes, gradient).

Step 3. 4-((1-Oxo-4-(2-(trifluoromethyl)phenyl)-2,3-dihydro-1H-inden-2-yl)methyl)benzoic acid In accordance with the procedure of Example 1, step 3, methyl 4-((1-oxo-4-(2-(trifluoromethyl)phenyl)-2,3-dihydro-1H-inden-2-yl)methyl)benzoate (11 mg, 0.026 mmol) was converted into 10 mg (94%) of the title compound.

Example 8

4-((4-(3-Methoxy-5-(trifluoromethyl)phenyl)-1-oxo-2,3-dihydro-1H-inden-2-yl)methyl)benzoic acid Step 1. 4-(3-Methoxy-5-(trifluoromethyl)phenyl)-2,3-dihydro-1H-inden-1-one In accordance with the procedure of Example 1, step 1, 4-bromo-2,3-dihydro-1H-inden-1-one (4-bromo-1-indanone, 211 mg, 1.0 mmol) and 3-methoxy-5-(trifluoromethyl)phenyl boronic acid (264 mg, 1.2 mmol) were converted into 200 mg (65%) of 4-(3-methoxy-5-(trifluoromethyl)phenyl)-2,3-dihydro-1H-inden-1-one after combiflash purification (40 g column, hexanes→40% EtOAc/hexanes, gradient).

Step 2. Methyl 4-((4-(3-methoxy-5-(trifluoromethyl)phenyl)-1-oxo-2,3-dihydro-1H-inden-2-yl)methyl)benzoate In accordance with the procedure of Example 4, step 2, 4-(3-methoxy-5-(trifluoromethyl)phenyl)-2,3-dihydro-1H-inden-1-one (200 mg, 0.65 mmol) and methyl 4-(bromomethyl)benzoate (153 mg, 0.67 mmol) were converted into 20 mg (7%) of methyl 4-((4-(3-methoxy-5-(trifluoromethyl)phenyl)-1-oxo-2,3-dihydro-1H-inden-2-yl)methyl)benzoate after combiflash purification (40 g column, hexanes→35% EtOAc/hexanes, gradient).

Step 3. 4-((4-((4-(3-Methoxy-5-(trifluoromethyl)phenyl)-1-oxo-2,3-dihydro-1H-inden-2-yl)methyl)benzoic acid In accordance with the procedure of Example 1, step 3, methyl 4-((4-(3-methoxy-5-(trifluoromethyl)phenyl)-1-oxo-2,3-dihydro-1H-inden-2-yl)methyl)benzoate (10 mg, 0.022 mmol) was converted into 9 mg (93%) of the title compound.

Example 9

4-((4-(3,5-Bis(trifluoromethyl)phenyl)-1-oxo-2,3-dihydro-1H-inden-2-yl)methyl)benzoic acid Step 1. 4-(3,5-Bis(trifluoromethyl)phenyl)-2,3-dihydro-1H-inden-1-one In accordance with the procedure of Example 1, step 1, 4-bromo-2,3-dihydro-1H-inden-1-one (4-bromo-1-indanone, 211 mg, 1.0 mmol) and 3,5-bis(trifluoromethyl)phenyl boronic acid (310 mg, 1.2 mmol) were converted into 333 mg (97%) of 4-(3,5-bis(trifluoromethyl)phenyl)-2,3-dihydro-1H-inden-1-one after combiflash purification (40 g column, hexanes→30% EtOAc/hexanes, gradient).

Step 2. Methyl 4-((4-(3,5-bis(trifluoromethyl)phenyl)-1-oxo-2,3-dihydro-1H-inden-2-yl)methyl)benzoate In accordance with the procedure of Example 4, step 2, 4-(3,5-bis(trifluoromethyl)phenyl)-2,3-dihydro-1H-inden-1-one (207 mg, 0.60 mmol) and methyl 4-(bromomethyl)benzoate (142 mg, 0.62 mmol) were converted into 32 mg (11%) of methyl 4-((4-(3,5-bis(trifluoromethyl)phenyl)-1-oxo-2,3-dihydro-1H-inden-2-yl)methyl)benzoate after combiflash purification (40 g column, hexanes→35% EtOAc/hexanes, gradient).

Step 3. 4-((4-(3,5-Bis(trifluoromethyl)phenyl)-1-oxo-2,3-dihydro-1H-inden-2-yl)methyl)benzoic acid In accordance with the procedure of Example 1, step 3, 4-((4-(3,5-bis(trifluoromethyl)phenyl)-1-oxo-2,3-dihydro-1H-inden-2-yl)methyl)benzoic acid (10 mg, 0.02 mmol) was converted into 9 mg (93%) of the title compound.

Example 10

4-((4-(4-Chloro-3-(trifluoromethyl)phenyl)-1-oxo-2,3-dihydro-1H-inden-2-yl)methyl)benzoic acid

Step 1. 4-(4-Chloro-3-(trifluoromethyl)phenyl)-2,3-dihydro-1H-inden-1-one

In accordance with the procedure of Example 1, step 1, 4-bromo-2,3-dihydro-1H-inden-1-one (4-bromo-1-indanone, 211 mg, 1.0 mmol) and 4-chloro-3-(trifluoromethyl)phenyl boronic acid (270 mg, 1.2 mmol) were converted into 290 mg (93%) of 4-(4-chloro-3-(trifluoromethyl)phenyl)-2,3-dihydro-1H-inden-1-one after combiflash purification (40 g column, hexanes→30% EtOAc/hexanes, gradient).

Step 2. Methyl 4-((4-(4-chloro-3-(trifluoromethyl)phenyl)-1-oxo-2,3-dihydro-1H-inden-2-yl)methyl)benzoate In accordance with the procedure of Example 4, step 2, 4-(4-chloro-3-(trifluoromethyl)phenyl)-2,3-dihydro-1H-inden-1-one (187 mg, 0.60 mmol) and methyl 4-(bromomethyl)benzoate (142 mg, 0.62 mmol) were converted into 18 mg (7%) of methyl 4-((4-(4-chloro-3-(trifluoromethyl)phenyl)-1-oxo-2,3-dihydro-1H-inden-2-yl)methyl)benzoate after combiflash purification (40 g column, hexanes→30% EtOAc/hexanes, gradient).

Step 3. 4-((4-(4-Chloro-3-(trifluoromethyl)phenyl)-1-oxo-2,3-dihydro-1H-inden-2-yl)methyl)benzoic acid In accordance with the procedure of Example 1, step 3, methyl 4-((4-(4-chloro-3-(trifluoromethyl)phenyl)-1-oxo-2,3-dihydro-1H-inden-2-yl)methyl)benzoate (9 mg, 0.02 mmol) was converted into 8 mg (92%) of the title compound.

Example 11

4-((4-(3-Methoxyphenyl)-1-oxo-2,3-dihydro-1H-inden-2-yl)methyl)benzoic acid

Step 1. 4-(3-Methoxyphenyl)-2,3-dihydro-1H-inden-1-one

In accordance with the procedure of Example 1, step 1, 4-bromo-2,3-dihydro-1H-inden-1-one (4-bromo-1-indanone, 211 mg, 1.0 mmol) and 3-methoxyphenyl boronic acid (183 mg, 1.2 mmol) were converted into 220 mg (92%) of 4-(3-methoxyphenyl)-2,3-dihydro-1H-inden-1-one after combiflash purification (40 g column, hexanes→25% EtOAc/hexanes, gradient).

Step 2. Methyl 4-((4-(3-methoxyphenyl)-1-oxo-2,3-dihydro-1H-inden-2-yl)methyl)benzoate In accordance with the procedure of Example 4, step 2, 4-(3-methoxyphenyl)-2,3-dihydro-1H-inden-1-one (143 mg, 0.60 mmol) and methyl 4-(bromomethyl)benzoate (142 mg, 0.62 mmol) were converted into 21 mg (9%) of methyl 4-((4-(3-methoxyphenyl)-1-oxo-2,3-dihydro-1H-inden-2-yl)methyl)benzoate after combiflash purification (40 g column, hexanes→25% EtOAc/hexanes, gradient).

Step 3. 4-((4-(3-Methoxyphenyl)-1-oxo-2,3-dihydro-1H-inden-2-yl)methyl)benzoic acid In accordance with the procedure of Example 1, step 3, using a modified reaction temperature of 45° C., methyl 4-((4-(3-methoxyphenyl)-1-oxo-2,3-dihydro-1H-inden-2-yl)methyl)benzoate (10 mg, 0.026 mmol) was converted into 8 mg (83%) of the title compound.

Example 12

4-((1-Oxo-4-(m-tolyl)-2,3-dihydro-1H-inden-2-yl)methyl)benzoic acid

Step 1. 4-(m-Tolyl)-2,3-dihydro-1H-inden-1-one

In accordance with the procedure of Example 1, step 1, 4-bromo-2,3-dihydro-1H-inden-1-one (4-bromo-1-indanone, 211 mg, 1.0 mmol) and m-tolylboronic acid (163 mg, 1.2 mmol) were converted into 215 mg (97%) of 4-(m-tolyl)-2,3-dihydro-1H-inden-1-one after combiflash purification (40 g column, hexanes→25% EtOAc/hexanes, gradient).

Step 2. Methyl 4-((1-oxo-4-(m-tolyl)-2,3-dihydro-1H-inden-2-yl)methyl)benzoate In accordance with the procedure of Example 4, step 2, 4-(m-tolyl)-2,3-dihydro-1H-inden-1-one (133 mg, 0.60 mmol) and methyl 4-(bromomethyl)benzoate (142 mg, 0.62 mmol) were converted into 33 mg (15%) of methyl 4-((1-oxo-4-(m-tolyl)-2,3-dihydro-1H-inden-2-yl)methyl)benzoate after combiflash purification (40 g column, hexanes→25% EtOAc/hexanes, gradient).

Step 3. 4-((1-Oxo-4-(m-tolyl)-2,3-dihydro-1H-inden-2-yl)methyl)benzoic acid In accordance with the procedure of Example 1, step 3, using a modified reaction temperature of 45° C., methyl 4-((1-oxo-4-(m-tolyl)-2,3-dihydro-1H-inden-2-yl)methyl)benzoate (11 mg, 0.03 mmol) was converted into 10 mg (94%) of the title compound.

Example 13

4-((1-Oxo-4-phenyl-2,3-dihydro-1H-inden-2-yl)methyl)benzoic acid

Step 1. 4-Phenyl-2,3-dihydro-1H-inden-1-one

In accordance with the procedure of Example 1, step 1, 4-bromo-2,3-dihydro-1H-inden-1-one (4-bromo-1-indanone, 211 mg, 1.0 mmol) and phenyl boronic acid (146 mg, 1.2 mmol) were converted into 185 mg (89%) of 4-phenyl-2,3-dihydro-1H-inden-1-one after combiflash purification (40 g column, hexanes→25% EtOAc/hexanes, gradient).

Step 2. Methyl 4-((1-oxo-4-phenyl-2,3-dihydro-1H-inden-2-yl)methyl)benzoate In accordance with the procedure of Example 4, step 2, 4-phenyl-2,3-dihydro-1H-inden-1-one (125 mg, 0.60 mmol) and methyl 4-(bromomethyl)benzoate (142 mg, 0.62 mmol) were converted into 40 mg (19%) of methyl 4-((1-oxo-4-phenyl-2,3-dihydro-1H-inden-2-yl)methyl)benzoate after combiflash purification (40 g column, hexanes→25% EtOAc/hexanes, gradient).

Step 3. 4-((1-Oxo-4-phenyl-2,3-dihydro-1H-inden-2-yl)methyl)benzoic acid

In accordance with the procedure of Example 1, step 3, using a modified reaction temperature of 45° C., methyl 4-((1-oxo-4-phenyl-2,3-dihydro-1H-inden-2-yl)methyl)benzoate (11 mg, 0.03 mmol) was converted into 10 mg (95%) of the title compound.

Example 14

5-((1-Oxo-5-(3-(trifluoromethyl)phenyl)-1,2,3,4-tetrahydronaphthalen-2-yl)methyl)thiophene-2-carboxylic acid Step 1. Methyl 5-(1-oxo-5-(3-(trifluoromethyl)phenyl)-1,2,3,4-tetrahydronaphthalen-2-yl)methyl)thiophene-2-carboxylate In accordance with the procedure of Example 4, step 2, 5-(3-(trifluoromethyl)phenyl)-3,4-dihydronaphthalen-1(2H)-one (180 mg, 0.62 mmol) and methyl 5-(bromomethyl)thiophene-2-carboxylate (150 mg, 0.64 mmol) were converted into 30 mg (11%) of methyl 5-((1-oxo-5-(3-(trifluoromethyl)phenyl)-1,2,3,4-tetrahydronaphthalen-2-yl)methyl)thiophene-2-carboxylate after combiflash purification (40 g column, hexanes→30% EtOAc/hexanes, gradient).

Step 2. 5-((1-Oxo-5-(3-(trifluoromethyl)phenyl)-1,2,3,4-tetrahydronaphthalen-2-yl)methyl)thiophene-2-carboxylic acid In accordance with the procedure of Example 1, step 3, using a modified reaction temperature of 50° C., methyl 5-((1-oxo-5-(3-(trifluoromethyl)phenyl)-1,2,3,4-tetrahydronaphthalen-2-yl)methyl)thiophene-2-carboxylate (9 mg, 0.02 mmol) was converted into 8 mg (92%) of the title compound.

Example 15

5-((1-Oxo-4-(3-(trifluoromethyl)phenyl)-2,3-dihydro-1H-inden-2-yl)methyl)thiophene-2-carboxylic acid Step 1. Methyl 5-((1-oxo-4-(3-(trifluoromethyl)phenyl)-2,3-dihydro-1H-inden-2-yl)methyl)thiophene-2-carboxylate In accordance with the procedure of Example 4, step 2, 4-(3-(trifluoromethyl)phenyl)-2,3-dihydro-1H-inden-1-one (166 mg, 0.60 mmol) and methyl 5-(bromomethyl)thiophene-2-carboxylate (145 mg, 0.62 mmol) were converted into 17 mg (6%) of methyl 5-((1-oxo-4-(3-(trifluoromethyl)phenyl)-2,3-dihydro-1H-inden-2-yl)methyl)thiophene-2-carboxylate after two combiflash purifications (40 g, hexanes→30% EtOAc/hexanes, gradient; then 4 g, hexanes→30% EtOAc/hexanes, gradient).

Step 2. 5-((1-Oxo-4-(3-(trifluoromethyl)phenyl)-2,3-dihydro-1H-inden-2-yl)methyl)thiophene-2-carboxylic acid In accordance with the procedure of Example 1, step 3, using a modified reaction temperature of 50° C., methyl 5-((1-oxo-4-(3-(trifluoromethyl)phenyl)-2,3-dihydro-1H-inden-2-yl)methyl)thiophene-2-carboxylate (9 mg, 0.021 mmol) was converted into 8 mg (92%) of the title compound.

Example 16

5-((4-(3-Chlorophenyl)-1-oxo-2,3-dihydro-1H-inden-2-yl)methyl)thiophene-2-carboxylic acid Step 1. Methyl 5-((4-(3-chlorophenyl)-1-oxo-2,3-dihydro-1H-inden-2-yl)methyl)thiophene-2-carboxylate In accordance with the procedure of Example 4, step 2, 4-(3-chlorophenyl)-2,3-dihydro-1H-inden-1-one (140 mg, 0.58 mmol) and methyl 5-(bromomethyl)thiophene-2-carboxylate (135 mg, 0.57 mmol) were converted into 3 mg (1%) of methyl 5-((4-(3-chlorophenyl)-1-oxo-2,3-dihydro-1H-inden-2-yl)methyl)thiophene-2-carboxylate after combiflash purification (40 g silica, hexanes→30% EtOAc/hexanes, gradient).

Step 2. 5-((4-(3-Chlorophenyl)-1-oxo-2,3-dihydro-1H-inden-2-yl)methyl)thiophene-2-carboxylic acid In accordance with the procedure of Example 1, step 3, using a modified reaction temperature of 60° C., methyl 5-((4-(3-chlorophenyl)-1-oxo-2,3-dihydro-1H-inden-2-yl)methyl)thiophene-2-carboxylate (3 mg, 0.008 mmol) was converted into 2.5 mg (86%) of the title compound.

Example 17

4-((1-Oxo-4-(3-(trifluoromethyl)phenyl)-2,3-dihydro-1H-inden-2-yl)methyl)thiophene-2-carboxylic acid Step 1. Methyl 4-((1-oxo-4-(3-(trifluoromethyl)phenyl)-2,3-dihydro-1H-inden-2-yl)methyl)thiophene-2-carboxylate In accordance with the procedure of Example 4, step 2, 4-(3-(trifluoromethyl)phenyl)-2,3-dihydro-1H-inden-1-one (166 mg, 0.60 mmol) and methyl 4-(bromomethyl)thiophene-2-carboxylate (145 mg, 0.62 mmol) were converted into 40 mg (15%) of methyl 4-((1-oxo-4-(3-(trifluoromethyl)phenyl)-2,3-dihydro-1H-inden-2-yl)methyl)thiophene-2-carboxylate after combiflash purification (40 g column, hexanes→30% EtOAc/hexanes, gradient).

Step 2. 4-((1-Oxo-4-(3-(trifluoromethyl)phenyl)-2,3-dihydro-1H-inden-2-yl)methyl)thiophene-2-carboxylic acid In accordance with the procedure of Example 1, step 3, using a modified reaction temperature of 50° C., methyl 4-((1-oxo-4-(3-(trifluoromethyl)phenyl)-2,3-dihydro-1H-inden-2-yl)methyl)thiophene-2-carboxylate (9 mg, 0.021 mmol) was converted into 8.5 mg (98%) of the title compound.

Example 18

5-((1-Oxo-4-(3-(trifluoromethyl)phenyl)-2,3-dihydro-1H-inden-2-yl)methyl)thiophene-3-carboxylic acid Step 1. Methyl 5-((1-oxo-4-(3-(trifluoromethyl)phenyl)-2,3-dihydro-1H-inden-2-yl)methyl)thiophene-3-carboxylate In accordance with the procedure of Example 4, step 2, 4-(3-(trifluoromethyl)phenyl)-2,3-dihydro-1H-inden-1-one (166 mg, 0.60 mmol) and methyl 5-(bromomethyl) thiophene-3-carboxylate (145 mg, 0.62 mmol) were converted into 11 mg (4%) of methyl 5-((1-oxo-4-(3-(trifluoromethyl)phenyl)-2,3-dihydro-1H-inden-2-yl)methyl) thiophene-3-carboxylate after combiflash purification (40 g column, hexanes→30% EtOAc/hexanes, gradient).

Step 2. 5-((1-Oxo-4-(3-(trifluoromethyl)phenyl)-2,3-dihydro-1H-inden-2-yl)methyl)thiophene-3-carboxylic acid In accordance with the procedure of Example 1, step 3, using a modified reaction temperature of 50° C., methyl 5-((1-oxo-4-(3-(trifluoromethyl)phenyl)-2,3-dihydro-1H-inden-2-yl)methyl)thiophene-3-carboxylate (11 mg, 0.026 mmol) was converted into 10 mg (94%) of the title compound.

Example 19

3-((1-Oxo-4-(3-(trifluoromethyl)phenyl)-2,3-dihydro-1H-inden-2-yl)methyl)benzoic acid Step 1. Methyl 3-((1-oxo-4-(3-(trifluoromethyl)phenyl)-2,3-dihydro-1H-inden-2-yl)methyl)benzoate In accordance with the procedure of Example 4, step 2, 4-(3-(trifluoromethyl)phenyl)-2,3-dihydro-1H-inden-1-one (108 mg, 0.39 mmol) and methyl 3-(bromomethyl)benzoate (92 mg, 0.40 mmol) were converted into 8 mg (5%) of methyl 3-((1-oxo-4-(3-(trifluoromethyl)phenyl)-2,3-dihydro-1H-inden-2-yl)methyl)benzoate after combiflash purification (12 g column, hexanes→30% EtOAc/hexanes, gradient).

Step 2. 3-((1-Oxo-4-(3-(trifluoromethyl)phenyl)-2,3-dihydro-1H-inden-2-yl)methyl)benzoic acid In accordance with the procedure of Example 1, step 3, using a modified reaction temperature of 45° C., methyl 3-((1-oxo-4-(3-(trifluoromethyl)phenyl)-2,3-dihydro-1H-inden-2-yl)methyl)benzoate (8 mg, 0.019 mmol) was converted into 7 mg (90%) of the title compound.

Example 20

4-((7-Methoxy-1-oxo-4-(3-(trifluoromethyl)phenyl)-2,3-dihydro-1H-inden-2-yl)methyl)benzoic acid Step 1. 7-Methoxy-4-(3-(trifluoromethyl)phenyl)-2,3-dihydro-1H-inden-1-one In accordance with the procedure of Example 1, step 1, 4-bromo-7-methoxy-2,3-dihydro-1H-inden-1-one (523 mg, 2.17 mmol) and 3-trifluoromethylphenyl boronic acid (489 mg, 2.57 mmol) were converted into 630 mg (95%) of 7-methoxy-4-(3-(trifluoromethyl)phenyl)-2,3-dihydro-1H-inden-1-one after combiflash purification (40 g column, hexanes→60% EtOAc/hexanes, gradient).

Step 2. Methyl 7-methoxy-1-oxo-4-(3-(trifluoromethyl)phenyl)-2,3-dihydro-1H-indene-2-carboxylate A solution of lithium diisopropylamide (2.0 M in THF, 0.18 mL, 0.36 mmol) was added to a solution of 7-methoxy-4-(3-(trifluoromethyl)phenyl)-2,3-dihydro-1H-inden-1-one (103 mg, 0.34 mmol) in THF (1.1 mL) at −78° C. After 1 h at −78° C., methyl cyanoformate (40 µL, 0.50 mmol) was added and the reaction mixture was allowed to warm to room temperature. After stirring at room temperature overnight, the reaction was quenched with saturated aqueous NH$_4$Cl (25 mL) and extracted with EtOAc (3×40 mL). The combined organic extracts were dried (Na$_2$SO$_4$), filtered and concentrated. The resulting crude residue was purified by combiflash (12 g column, hexanes→EtOAc, gradient) to afford 26 mg (21%) of methyl 7-methoxy-1-oxo-4-(3-(trifluoromethyl)phenyl)-2,3-dihydro-1H-indene-2-carboxylate.

Step 3. Methyl 7-methoxy-2-(4-(methoxycarbonyl)benzyl)-1-oxo-4-(3-(trifluoromethyl)phenyl)-2,3-dihydro-1H-indene-2-carboxylate Potassium carbonate (15 mg, 0.11 mmol) was added to a solution of methyl 7-methoxy-1-oxo-4-(3-(trifluoromethyl)phenyl)-2,3-dihydro-1H-indene-2-carboxylate (26 mg, 0.07 mmol) in acetone (1.0 mL). Methyl 4-(bromomethyl)benzoate (32 mg, 0.14 mmol) was added and the mixture was stirred at room temperature. After 4 d, the reaction mixture was diluted with water (10 mL) and extracted with EtOAc (3×20 mL). The combined organic extracts were dried (Na$_2$SO$_4$), filtered and concentrated. The resulting crude residue was purified by combiflash (4 g column, hexanes→EtOAc, gradient) to afford 36 mg (98%) of methyl 7-methoxy-2-(4-(methoxycarbonyl)benzyl)-1-oxo-4-(3-(trifluoromethyl)phenyl)-2,3-dihydro-1H-indene-2-carboxylate.

Step 4. 4-((7-Methoxy-1-oxo-4-(3-(trifluoromethyl)phenyl)-2,3-dihydro-1H-inden-2-yl)methyl)benzoic acid Aqueous lithium hydroxide (1 N, 1.0 mL, 1.0 mmol) was added to a solution of methyl 7-methoxy-2-(4-(methoxycarbonyl)benzyl)-1-oxo-4-(3-(trifluoromethyl)phenyl)-2,3-dihydro-1H-indene-2-carboxylate (36 mg, 0.071 mmol) in THF (1.0 mL) in a scintillation vial. The vial was sealed under nitrogen and heated at 60° C. After 24 h, the reaction mixture was allowed to cool and the volatiles were evaporated under a stream of nitrogen. The residue was diluted with water (5.0 mL), acidified with 1 N aqueous HCl (2.0 mL) and extracted with EtOAc (3×20 mL). The combined organic extracts were dried (Na$_2$SO$_4$), filtered and concentrated in vacuo. The resulting crude residue was purified by combiflash (4 g column, CH$_2$Cl$_2$→20% MeOH/CH$_2$Cl$_2$, gradient). All fractions containing the desired product were combined and the resulting crude product was further purified by preparative thin layer chromatography (1000 µM thickness, EtOAc), to afford 8 mg (26%) of the title compound.

While this invention has been described with respect to these specific examples, it is understood that other modifications and variations are possible without departing from the spirit of the invention.

What is claimed is:
1. A compound having the structure:

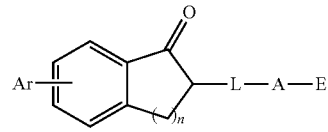

wherein:
Ar is aryl, heteroaryl, substituted aryl, or substituted heteroaryl, wherein substituents are selected from alkyl, alkenyl, alkynyl, hydroxyalkyl, hydroxyl, alkoxy, halogen, —CN, —CF$_3$, —C(O)R$^1$, —C(O)OR$^1$, —C(O)CF$_3$, —SO$_2$N(R$^1$)$_2$, —SO$_2$NH$_2$, or —NO$_2$;

L is C$_1$-C$_6$ alkylene;

A is arylene or heteroarylene;

E is —CO$_2$R$^1$, —CH$_2$OR$^1$, —C(O)N(R$^1$)$_2$, or tetrazol-5-yl;

each R$^1$ is independently H, C$_1$-C$_6$ alkyl, phenyl, or biphenyl; and n is 0 or 1;

or a pharmaceutically acceptable salt thereof.

2. The compound of claim 1, wherein Ar is substituted or unsubstituted phenyl or naphthyl.

3. The compound of claim 1, wherein the substituents are halogen, alkoxy, or —CF$_3$.

4. The compound of claim 1, wherein L is C$_1$-C$_3$ alkylene.

5. The compound of claim 1, wherein L is methylene.

6. The compound of claim 1, wherein A is phenylene or thiophenylene.

7. The compound of claim 1, wherein E is —CO$_2$R$^1$.

8. The compound of claim 7, wherein R$^1$ is H or C$_1$-C$_6$ alkyl.

9. A pharmaceutical composition comprising at least one compound according to claim 1, and a pharmaceutically acceptable carrier therefor.

10. The compound of claim 1 selected from the group consisting of:

-continued
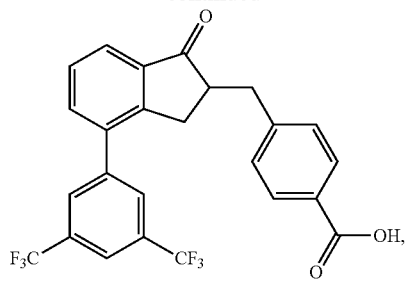
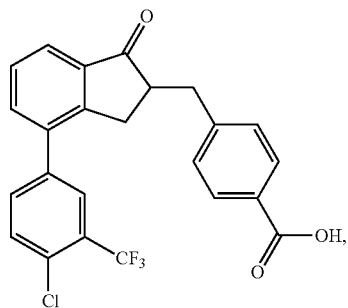
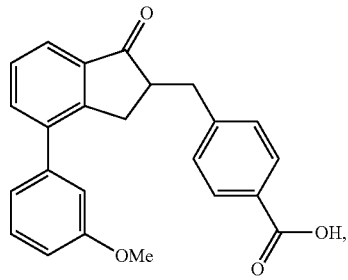
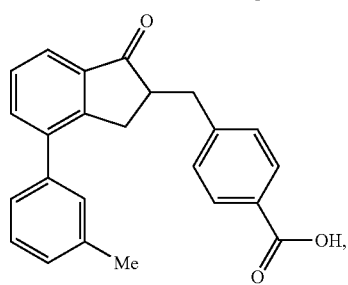
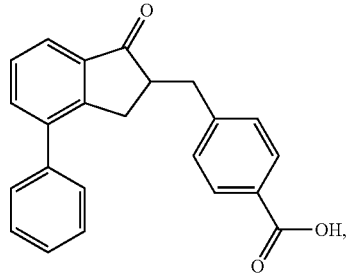
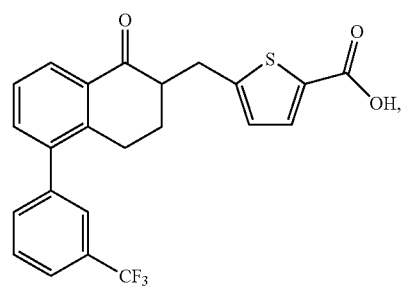
-continued
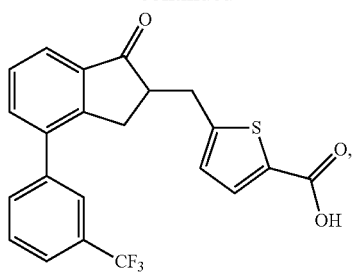
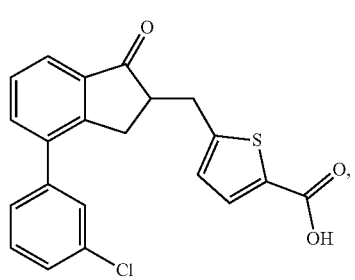
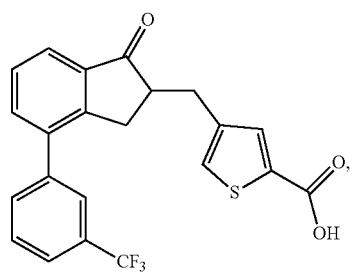
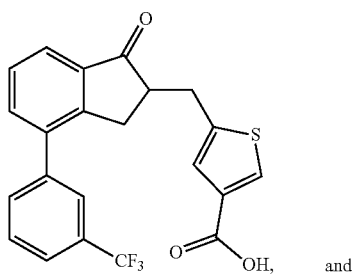
and
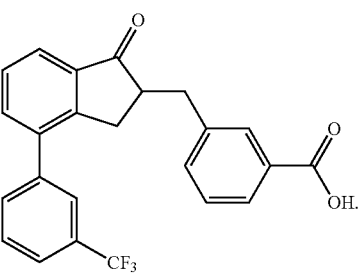

11. A compound having the structure:
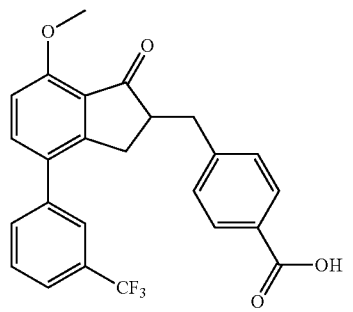 [SMILES: COc1ccc(-c2cccc(C(F)(F)F)c2)c2c1C(=O)C(Cc1ccc(C(=O)O)cc1)C2]
or a pharmaceutically acceptable salt thereof.
* * * * *